US011229608B2

(12) United States Patent
Santra et al.

(10) Patent No.: US 11,229,608 B2
(45) Date of Patent: Jan. 25, 2022

(54) COMPOSITIONS AND METHODS FOR SYSTEMIC DELIVERY OF CARGOS IN VASCULAR PLANTS

(71) Applicants: UNIVERSITY OF CENTRAL FLORIDA RESEARCH FOUNDATION, INC., Orlando, FL (US); ICAR-CENTRAL CITRUS RESEARCH INSTITUTE, Maharashtra (IN); INDIAN INSTITUTE OF TECHNOLOGY ROORKEE, Uttarakhand (IN)

(72) Inventors: Swadeshmukul Santra, Oviedo, FL (US); Ali Ozcan, Orlando, FL (US); Dilip K. Ghosh, Maharashtra (IN); Sunil Kokane, Maharashtra (IN); Pranav Kumar, Uttarakhand (IN); Ashwani Kumar Sharma, Uttarakhand (IN)

(73) Assignees: University of Central Florida Research Foundation, Inc., Orlando, FL (US); ICAR-Central Citrus Research Institute, Maharashtra (IN); Indian Institute Technology ROORKEE, Uttarakhand (IN)

( * ) Notice: Subject to any disclaimer, the term of this patent is extended or adjusted under 35 U.S.C. 154(b) by 0 days.

(21) Appl. No.: 16/776,014

(22) Filed: Jan. 29, 2020

(65) Prior Publication Data

US 2020/0237677 A1 Jul. 30, 2020

Related U.S. Application Data

(60) Provisional application No. 62/798,116, filed on Jan. 29, 2019.

(51) Int. Cl.
*A61K 9/51* (2006.01)
*A61K 9/50* (2006.01)
*A61K 38/16* (2006.01)

(52) U.S. Cl.
CPC .......... *A61K 9/5115* (2013.01); *A61K 9/5015* (2013.01); *A61K 38/168* (2013.01)

(58) Field of Classification Search
CPC .............................. A61K 9/5115; A01N 25/12
See application file for complete search history.

(56) References Cited

U.S. PATENT DOCUMENTS

2017/0246353 A1* 8/2017 Yang ...................... A61L 27/34

OTHER PUBLICATIONS

Wu et al., Current Applied Phys, 14, 2014, 1470-1475.*
Neto et al., Protein J, 2011, 30, 340-350.*
Hamed et al. (Int J Adv Res Biol Sci, 2(12), 2015, 45-59.*
Ancona, Andrea et al., "Lipid-Coated Zinc Oxide Nanoparticles as Innovative ROS-Generators for Photodynamic Therapy in Cancer Cells", Nanomaterials, 2018, vol. 8, No. 143, 15 pages.
Bera, Debasis et al., "Photoluminescence of ZnO quantum dots produced by a sol-gel process", Optical Materials, 2008, vol. 30, pp. 1233-1239.
Chauhan, Preeti et al., "A Cytocompatible Zinc Oxide Nanocomposite Loaded with an Amphiphilic Arsenal for Alleviation of *Staphylococcus* Biofilm", Chemistry Select, 2018, vol. 3, pp. 2492-2497.
Fakhar-E-Alam, M. et al, "ZnO nanoparticles as drug delivery agent for photodynamic therapy", Laser Physics Letters, 2014, vol. 11, 7 pages.
Ghosh, Dilip Kumar et al., "Antimicrobial nano-zinc oxide-2S albumin protein formulation significantly inhibits growth of Candidatus Liberibacter asiaticus" in planta, PLOS One, Oct. 10, 2018, 20 pages.
Huang, Xiao et al., "ZnO-based nanocarriers for drug delivery application: From passive to smart strategies", Internation Journal of Pharmaceutics, 2017, vol. 534, pp. 190-194.
Khalid, Ayesha et al., "Bacterial cellulose-zinc oxide nanocomposites as a novel dressing system for burn wounds", Carbohydrate Plymers, 2017, vol. 164, pp. 214-221.
Kodoth, Arun K. et al., "Application of pectin zinc oxide hybrid nanocomposite in the delivery of a hydrophilic drug and a study of its isotherm, kinetics and release mechanism", International Journal of Biological Macromolecules, 2018, vol. 115, pp. 418-430.
Palanikumar, L. et al., "Influence of particle size of nano zinc oxide on the controlled delivery of Amoxicillin", Applied Nanoscience, 2013, vol. 3, pp. 441-451.
Soleymani, Safoura et al., "ZnO nanofluids for the improved cytotoxicity and cellular uptake of doxorubicin", Nanomed. J. 2018, vol. 5, No. 1, pp. 27-35.
Tan, Licheng et al., "A novel thermal and pH responsive drug delivery system based on ZnO@PNIPAM hybrid nanoparticles", Materials Science and Engineering, 2014, C45, pp. 524-529.

* cited by examiner

*Primary Examiner* — Kyle A Purdy
(74) *Attorney, Agent, or Firm* — Timothy H. Van Dyke; Wolter Van Dyke Davis, PLLC

(57) ABSTRACT

Compositions and methods for systemic delivery of at least one cargo in a vascular plant. Compositions may include at least one cargo delivery particle, having a core and a shell; and at least one cargo disposed on the shell. The core may include at least one micronutrient. The shell may include a coating material. The at least one cargo delivery particle may have a size of less than about 10 nanometers. Methods may include administering an effective amount of the compositions to a plant.

6 Claims, 15 Drawing Sheets

Specification includes a Sequence Listing.

300

```
┌─────────────────────────────────────────────────┐
│ DISPERSE A SALT OF A MICRONUTRIENT IN A SOLUTION │ ~302
└─────────────────────────────────────────────────┘
                        │
                        ▼
┌─────────────────────────────────────────────────┐
│      ADD A COATING MATERIAL TO THE SOLUTION      │ ~304
└─────────────────────────────────────────────────┘
                        │
                        ▼
┌─────────────────────────────────────────────────┐
│ ALLOW COATING MATERIAL TO INTERACT WITH IONS OF  │ ~306
│               THE MICRONUTRIENT                  │
└─────────────────────────────────────────────────┘
                        │
                        ▼
┌─────────────────────────────────────────────────┐
│           RAISE THE PH OF THE SOLUTION           │ ~308
└─────────────────────────────────────────────────┘
                        │
                        ▼
┌─────────────────────────────────────────────────┐
│ ALLOW FORMATION OF CARGO DELIVERY PARTICLES      │
│ HAVING A CORE COMPRISING THE MICRONUTRIENT       │ ~310
│ AND A SHELL COMPRISING THE COATING MATERIAL      │
└─────────────────────────────────────────────────┘
                        │
                        ▼
┌─────────────────────────────────────────────────┐
│       PURIFY THE CARGO DELIVERY PARTICLES        │ ~312
└─────────────────────────────────────────────────┘
                        │
                        ▼
┌─────────────────────────────────────────────────┐
│        DRY THE CARGO DELIVERY PARTICLES          │ ~314
└─────────────────────────────────────────────────┘
```

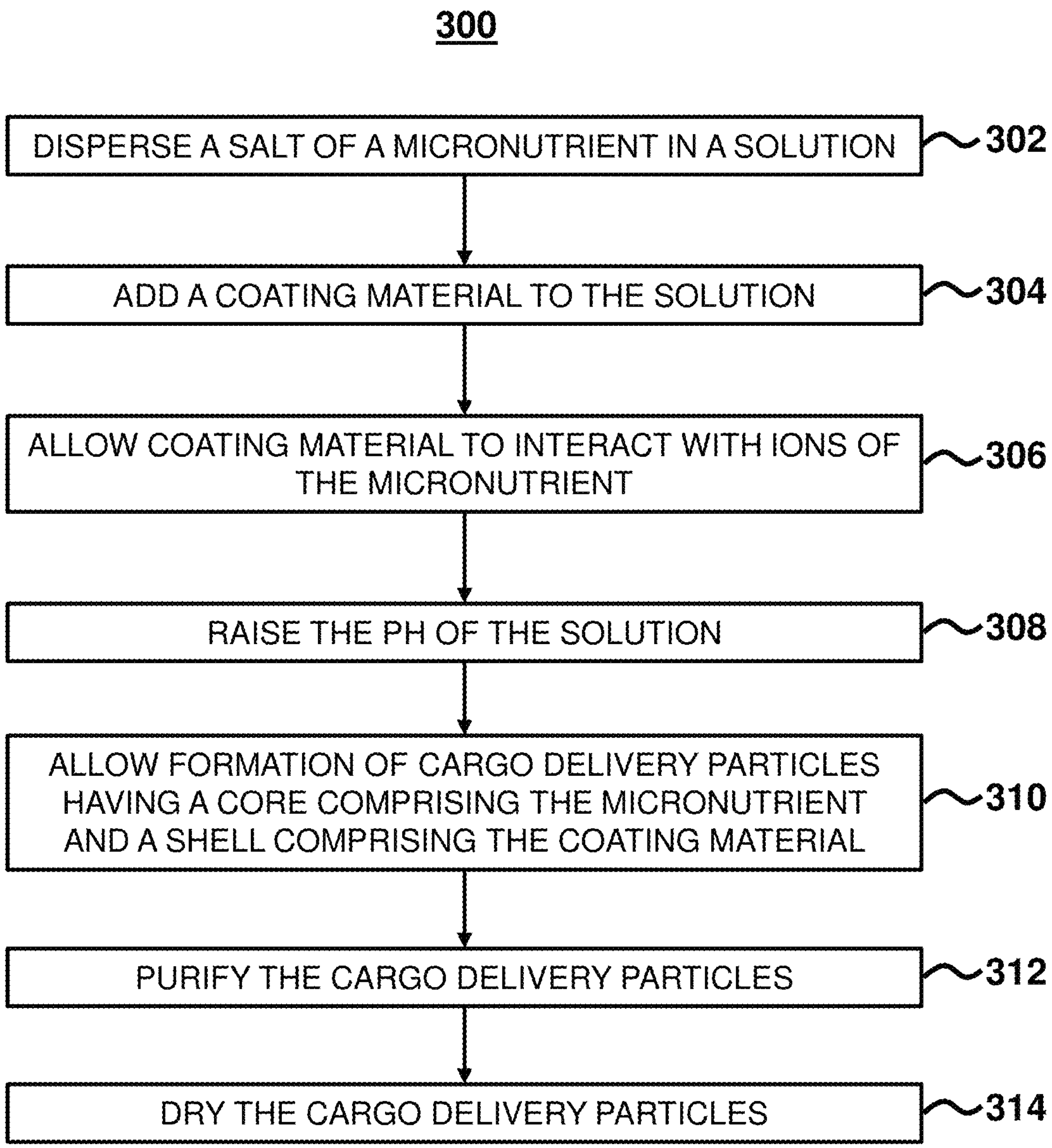

FIG. 3A

SEQUENCE LISTING

```
<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: primer sequence

<400> SEQUENCE: 1

tcgagcgcgt atgcaatacg                                                20


<210> SEQ ID NO 2
<211> LENGTH: 24
<212> TYPE: DNA
<213> ORGANISM: Artificial Sequence
<220> FEATURE:
<223> OTHER INFORMATION: primer sequence

<400> SEQUENCE: 2

gcgttatccc gtagaaaaag gtag                                           24


<210> SEQ ID NO 3
<211> LENGTH: 18
<212> TYPE: DNA
<213> ORGANISM: Artificial Sequence
<220> FEATURE:
<223> OTHER INFORMATION: primer sequence

<400> SEQUENCE: 3

agacgggtga gtaacgcg                                                  18


<210> SEQ ID NO 4
<211> LENGTH: 22
<212> TYPE: DNA
<213> ORGANISM: Artificial Sequence
<220> FEATURE:
```

-continued

```
<223> OTHER INFORMATION: primer sequence

<400> SEQUENCE: 4

gtatgccacg tcgcattcca ga                                          22


<210> SEQ ID NO 5
<211> LENGTH: 22
<212> TYPE: DNA
<213> ORGANISM: Artificial Sequence
<220> FEATURE:
<223> OTHER INFORMATION: primer sequence

<400> SEQUENCE: 5

gccaaaactc gtaagggcat tc                                          22


<210> SEQ ID NO 6
<211> LENGTH: 19
<212> TYPE: DNA
<213> ORGANISM: Artificial Sequence
<220> FEATURE:
<223> OTHER INFORMATION: primer sequence

<400> SEQUENCE: 6

atccagatgc ttacgctgg                                              19


<210> SEQ ID NO 7
<211> LENGTH: 20
<212> TYPE: DNA
<213> ORGANISM: Artificial Sequence
<220> FEATURE:
<223> OTHER INFORMATION: primer sequence

<400> SEQUENCE: 7

tcgagcgcgt atgcaatacg                                             20


<210> SEQ ID NO 8
<211> LENGTH: 20
<212> TYPE: DNA
<213> ORGANISM: Artificial Sequence
<220> FEATURE:
<223> OTHER INFORMATION: primer sequence

<400> SEQUENCE: 8

ctcgccccct tcgtattacc                                             20
```

COMPOSITIONS AND METHODS FOR SYSTEMIC DELIVERY OF CARGOS IN VASCULAR PLANTS

CROSS-REFERENCE TO RELATED APPLICATION

This application claims the benefit of U.S. Provisional Patent Application No. 62/798,116, filed Jan. 29, 2019, titled COATED NANO-ZNO AS THE SYSTEMIC DELIVERY SYSTEM FOR ANTIMICROBIAL BIOMOLECULES FOR CONTROLLING VASCULAR PLANT DISEASE, which is incorporated by reference herein in its entirety.

REFERENCE TO SEQUENCE LISTING

This application includes an electronically submitted sequence listing in .txt format. The .txt file contains a sequence listing entitled "10669280US1_ST5" created on Apr. 20, 2020 and is 2 kilobytes in size. The sequence listing contained in this .txt file is part of the specification and is hereby incorporated by reference herein in its entirety.

STATEMENT REGARDING FEDERALLY SPONSORED RESEARCH OR DEVELOPMENT

This invention was made with government support under USDA-NIFA CDRE grant #2015-70016-23010. The government has certain rights in this invention.

BACKGROUND

*Citrus* greening disease (Huanglongbing, HLB) is economically the most serious and fatal disease of *citrus* throughout the globe. The disease was first reported in China in 1919 and has since spread all over the world. The causal agent of HLB is a fastidious, gram-negative bacterium, which exists in nature mainly in the form of three species, viz. '*Candidatus Liberibacter asiaticus*' (CLas), '*Candidatus Liberibacter africanus*' (CLaf) and *Candidatus Liberibacter americanus* (CLam). Both CLas and CLam are vectored by *Diaphorina citri* Kuwayama and '*Candidatus* Liberibacter africanus' by the African *citrus* psyllid (*Trioza erytreae*), which is a sap-sucking insect, a hemipteran bug in the family Triozidae.

The three species of bacterium (CLas, CLaf, and CLam) are generally phloem-restricted and vectored by *citrus* psyllids. As used herein, the term "phloem-restricted" refers to a class of particles, here bacterium, having a particle size that results in limited accessibility to phloem tissue. The specific particle size required may vary from plant to plant. As referenced above, however, particles having sizes larger than 10 nm often have limited accessibility to phloem tissue and may, therefore, be classified as "phloem-restricted."

These causal agents of HLB propagate in the phloem tissue of host and are subsequently unevenly distributed throughout the plant. The bacterium induces the deposition of callose and P-protein plugs throughout the phloem elements of infected plants. Callose, for example, is a plant polysaccharide and may be produced to act as a temporary cell wall in response to stimuli such as stress or damage. The deposition of plugs has been observed in both lateral pit fields as well as in and around sieve plates, causing numerous pockets of necrotic phloem. These plugs create blockages and thereby hinder the translocation of photoassimilates from source to sink tissue. As a result, photoassimilates convert to starch in all CLas affected living cells, eliciting yellow shoots, blotchy mottles on leaves, shoot die-back, off-tasting and malformed fruits, eventually contributing to an average yield loss of 30-100%. It has been observed that as disease severity increases, the life span of infected *citrus* trees is reduced, and in severe cases the infected plants often die in 5 to 8 years.

The CLas bacteria are inaccessible for most antimicrobial and bactericidal agents; therefore, there is a lack of efficient control strategy at commercial level. There are no known *citrus* commercial cultivars with natural resistance against HLB.

There are limited control options available to the farmers that include elimination of psyllid vectors from the field using insecticides, reducing CLas inoculums by eradicating infected *citrus* plants from *citrus* groves and raising the HLB-free planting material in protected nurseries. The development of HLB tolerant *citrus* varieties is one of the most promising approaches, but unfortunately there is lack of HLB resistant genes. Some recent reports demonstrate reduction of CLas titer after treatment, i.e. graft-based chemotherapy, thermotherapy and use of antibiotics i.e. penicillin, carbenicillin and streptomycin. Several countries are trying to develop anti-HLB therapeutics involving injecting trees with different curative agents such as antimicrobials, bactericides and antibiotics to reduce the titer of CLas. However, the antibiotics treatment has adverse collateral effects i.e. appearance of antibiotic resistant bacteria and secondary delivery to consumers. Development of inhibitor molecules against CLas and generation of transgenic cultivars, to over-express the inhibitor molecule, would be a potent approach to control or manage HLB. Eleven SecA inhibitors have been reported and a micro-emulsion formulation has been developed for active delivery in planta. Recently, the HLB tolerant transgenic cultivars (Hamlin, Valencia) were developed, expressing NPR1 gene of Arabidopsis thaliana with a phloem specific SUC2 promoter. The effective treatment with Brassinosteroids against HLB has also been reported. However, this remediation treatment has not been used at the commercial level yet.

To date, there is no effective control available against CLas. To alleviate the effects of HLB on the industry and protect *citrus* farmers, there is an urgent need to identify or develop inhibitor molecules to suppress or eradicate CLas from infected *citrus* plant.

BRIEF SUMMARY

Various embodiments relate to a composition for systemic delivery of at least one cargo in a vascular plant, the composition may include at least one cargo delivery particle, having a core and a shell; and at least one cargo disposed on the shell of the cargo delivery particle. The core may include at least one metal micronutrient. The shell may include a coating material. The at least one cargo delivery particle may have a size of less than about 10 nanometers. The at least one metal micronutrient may include iron, copper, zinc, manganese, molybdenum, nickel, or a combination thereof. The coating material comprises N-acetylcysteine, salicylate, caffeine, or a combination thereof. The at least one cargo may include an agrichemical active ingredient, a biomolecule, a small molecule therapeutic (such as antibiotic), a metal, or a combination thereof.

For example, various embodiments may relate to an antimicrobial treatment composition for suppressing or preventing a plant pathogen in planta. The antimicrobial treatment composition may include at least one particle, having a core and a shell, and at least one antimicrobial 2S-albumin protein disposed on the shell. The core may include ZnO, and the shell may include N-Acetylcysteine (NAC). The plant pathogen may include *Candidatus* Liberibacter asiaticus (CLas), *Candidatus Liberibacter* africanus (CLaf), *Candidatus Liberibacter* americanus (CLam), or a combination thereof.

Various embodiments relate to a method for suppressing or preventing a plant pathogen in planta, the method may include administering an effective amount of the compositions according to the various embodiments to the plant.

For example, various embodiments relate to a method for delivery of a cargo to a vascular plant. The method may include administering a composition including the cargo and a cargo delivery particle to the vascular plant. The cargo delivery particle may have a core and a shell. The core may include at least one metal micronutrient. The shell may include a coating material. The cargo may be disposed on the shell of the cargo delivery particle. The composition may include a plurality of cargos and a plurality of cargo delivery particles. Each of the plurality of cargos may be disposed on the shell of one of the plurality of cargo delivery particles, and the method may results in systemic delivery of the plurality of cargos to the vascular plant.

These and other features, aspects, and advantages of various embodiments will become better understood with reference to the following description, Figures, and claims.

BRIEF DESCRIPTION OF THE FIGURES

Many aspects of this disclosure can be better understood with reference to the following Figures, in which:

FIG. 3A: is an example according to various embodiments illustrating a method for producing cargo delivery particles according to various embodiments;

Figure 1:
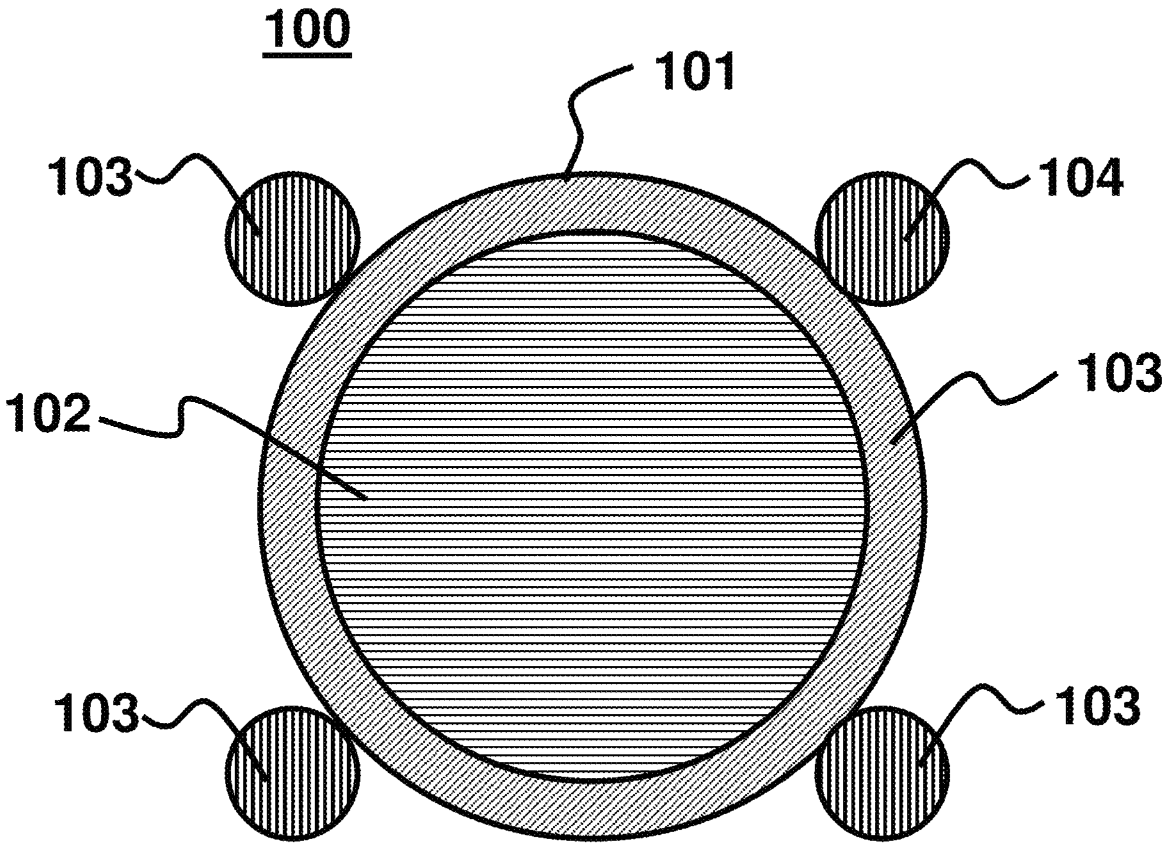
FIG. 1: is an example according to various embodiments illustrating a cargo delivery system for plants.

The various embodiments are not limited to the examples illustrated in the Figures.

DETAILED DESCRIPTION

Introduction and Definitions

Various embodiments may be understood more readily by reference to the following detailed description. Unless defined otherwise, all technical and scientific terms used herein have the same meaning as commonly understood by one of ordinary skill in the art to which this disclosure belongs.

The term "mol percent" or "mole percent" generally refers to the percentage that the moles of a particular component are of the total moles that are in a mixture. The sum of the mole fractions for each component in a solution is equal to 1.

It is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

All numeric values are herein assumed to be modified by the term "about," whether or not explicitly indicated. The term "about" generally refers to a range of numbers that one of skill in the art would consider equivalent to the recited value (i.e., having the same function or result). In many instances, the term "about" may include numbers that are rounded to the nearest significant figure.

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by prior disclosure. Further, the dates of publication provided could be different from the actual publication dates that may need to be independently confirmed.

Unless otherwise indicated, the present disclosure is not limited to particular materials, reagents, reaction materials, manufacturing processes, or the like, as such can vary. It is also to be understood that the terminology used herein is for purposes of describing particular embodiments only and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

As used herein the term "therapeutic benefit" is used to refer to suppression of one or more plant pathogens. A therapeutic benefit may be preventative or curative. For example, a therapeutic benefit may suppress a plant pathogen by strengthening a plant's resistance to the pathogen and/or by reducing the extent of a pre-existing infection of the plant pathogen.

As used herein the term "suppress or suppression" is used to mean changing the amount or rate of spread of a plant pathogen infection or reducing the extent of a plant pathogen infection.

As used herein the term "plant pathogen" relates to an organism (e.g. insect, bacteria, fungus, or virus) that infects a plant resulting in an adverse consequence in the plant and/or causes a plant disease.

All the features disclosed in this specification (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

The examples and embodiments described herein are for illustrative purposes only and that various modifications or changes in light thereof will be suggested to persons skilled in the art and are to be included within the spirit and purview of this application. Many variations and modifications may be made to the above-described embodiment(s) of the disclosure without departing substantially from the spirit and principles of the disclosure. All such modifications and variations are intended to be included herein within the scope of this disclosure.

Composition Comprising Cargo Delivery Particle(s) and Cargo(s)

FIG. 1 is an example according to various embodiments illustrating a composition 100 for plants. The composition 100 may include one or more cargo delivery particles 101 having a core 102 and a shell 103. The composition 100 may also include a cargo 104 or a plurality of cargos 104. It is noted that FIG. 1 is schematic and depicts substantially round cross-sectional structures for convenience of illustration and labeling; a person having ordinary skill in the art will readily appreciate that any three-dimensional shape or combination of three-dimensional shapes may be employed according to various embodiments. Elements of the composition 100 will be described in greater detail hereinafter.

Cargo Delivery Particle(s)

The cargo delivery particle 101 may deliver the one or more cargos 104 to previously unreachable or difficult to access areas of a plant, particularly via components of a plant's vasculature, thereby providing systemic delivery of the cargos 104. Such systemic delivery may provide a systemic effect, meaning that even if locally administered, one or more cargo delivery particles 101 and cargos 104 may ultimately be found in multiple tissues of the plant to which the composition 100 is administered. For example, according to various embodiments, despite being administered at a single location or at a limited number of locations of the plant, cargo delivery particles 100 and/or cargos 104 may ultimately be found in many tissues of the plant or even in every tissue of the plant. The cargos 104 may provide one or more therapeutic benefits to the plant. Additionally, according to various embodiments, the core 102 and/or the shell 103 may provide one or more therapeutic and/or nutritional benefits to the plant.

The compositions described herein provide significant advantages compared to administering the cargo alone. When administered alone, some cargoes may be bound to a plant enzyme and subsequently absorbed. When associated with a cargo delivery particle 101, according to various embodiments, however, the cargo is not 100% available immediately upon injection. The composition 100 may, therefore, provide improved systemic effect via a slow-release mechanism, whereby the cargo only becomes available for absorption after it is transported through the plant's vasculature. According to some embodiments, the dissolution rate of composition 100 may vary based on the plant type, on the in planta environment, as well as on various environmental conditions. Performance of compositions, may, therefore, vary based on geographical locations and plant type.

Prior to various embodiments described herein, efficient delivery of cargos to a plant's vasculature system, in particular to phloem tissue, was challenging. According to various embodiments, the cargo delivery particles 101 may be "protein-sized" as defined hereinafter. The cargo delivery particles 101 may, therefore, have a unique in planta mobility, enabling them to freely move to phloem tissue by passing through cambiums. Each of the cargos 104 may also be "protein-sized" as defined hereinafter. According to various embodiments, a "protein-sized" particle may have a size of less than about 10 nm or from about 2 nm to about 6 nm, or of less than about 5.4 nm. Each range described herein is intended to include all numerical values encompassed by the range. Furthermore, additional ranges may be formed from any lower limits and/or upper limits described herein. For example, a "protein-sized" particle may have a size within a range having a lower limit and/or an upper limit. The range may include or exclude the lower limit and/or the upper limit. By way of example and not limitation, a lower limit and/or an upper limit may be selected from 0.5, 1, 1.5, 2, 2.5, 3, 3.5, 4, 4.5, 5, 5.1, 5.2, 5.3, 5.4 5.5, 5.6, 5.7, 5.8, 5.9, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5 and 20 nm. A range formed from a single lower limit includes at least the lower limit and all numerical values greater than the lower limit regardless of whether the values are explicitly recited in this disclosure. A range formed from a single upper limit includes at least the upper limit and all numerical values less than the upper limit regardless of whether the values are explicitly recited in this disclosure. A range formed from a combination of a lower limit and an upper limit includes at least the lower limit, the upper limit, and all numerical values therebetween regardless of whether the values are explicitly recited in this disclosure. For example, based on the set of exemplary upper limits and lower limits explicitly recited above, a protein-sized particle may have a size of: about 0.5 to about 20 nm, less than about 0.5 nm, greater than about 0.5 nm, less than about 20 nm, or greater than about 20 nm, etc. All such ranges are contemplated and are intended to be explicitly disclosed and recited. Each value recited is intended to be modified by the term "about."

Core of the Cargo Delivery Particle(s)

Still referring to FIG. 1, the core 102 may include one or more micronutrients. The micronutrients may be, for example, metal micronutrients. Examples of metal micronutrients include, but are not limited to iron (Fe), copper (Cu), zinc (Zn), manganese (Mn), molybdenum (Mo), nickel (Ni), and various combinations thereof. Any combination of micronutrients may be employed. According to various embodiments, the metal micronutrient may be present in the core 102 in the form of a metal oxide, such as, for example, zinc oxide (ZnO), Zn hydroxide, Copper oxide, Copper hydroxide, Magnesium oxide, Magnesium hydroxide. The metal oxide may be present in any form. For example, zinc oxide may be present in any form, including hexagonal wurtzite and/or cubic zincblende. The core 102 may include a metal or a metal oxide in the form of one or more nanostructures. As used herein, the term "nanostructures" refers to materials having at least one dimension between about 1 to about 100 nm. A variety of nanostructures may be employed, including, for example, nanowires, nanorods, tetrapods, nanobelts, nanoflowers, and nanoparticles. A person having ordinary skill in the art will readily appreciate the morphologies of various nanostructures as well as how to produce them. As a specific example, the core 102 may include nanostructures of ZnO in a variety of morphologies including, but not limited to those listed above.

The "protein-sized" cargo delivery particles 101 having cores 102 comprising metal micronutrients, such as ZnO, may eventually degrade to metal ions, such as Zn ions, and become a part of the plant's micronutrient pool, contributing to productivity improvement. The cargo delivery particles 101, according to various embodiments, may be more soluble than fertilizer-grade bulk metal oxides, such as ZnO. due to increased surface area. The U.S. Food and Drug Administration (US FDA) listed ZnO as being generally recognized as safe (GRAS) if it is used as food additive. The U.S. Environmental Protection Agency (US EPA) has recently exempted ZnO (CAS Reg. No. 1314-13-2) from the requirement of tolerance when is used as an additive in an amount of up to 15% (wt/wt) in bactericide/fungicide formulations. A beneficial effect of ZnO (having a size of about 10 nm) on cucumber fruit (*Cucumis sativus*) was reported in greenhouse settings. As reported, soil application of ZnO at rates of 400 and 800 mg/kg did not demonstrate any negative effect on carbohydrate and antioxidant contents, but increased starch and protein content in comparison to untreated controls. According to various embodiments, ZnO may also provide various antimicrobial properties. For example, ZnO may provide effective antibacterial activity against gram-negative bacteria *Escherichia coli, Xanthomonas alfalfa, Pseudomonas aeruginosa*, and gram-positive bacteria *Staphylococcus aureus*. Detailed mechanisms of antimicrobial activity of ZnO have not been fully understood yet. Suggested mechanisms of killing are linked to release of antimicrobial zinc ions and production of reactive oxygen species.

The core 102 may additionally or alternatively comprise carbon-based nanomaterials such as carbon nanotubes, or nano-onions, which may further contribute to productivity increases, presumably due to their activity as plant stimulant.

According to various embodiments, the core may contain the metal micronutrient in an amount of from about 1 to about 5% by weight. Each range described herein is intended to include all numerical values encompassed by the range.

Furthermore, additional ranges may be formed from any lower limits and/or upper limits described herein. For example, according to various embodiments, the core may contain the metal micronutrient in an amount within a range having a lower limit and/or an upper limit. The range may include or exclude the lower limit and/or the upper limit. By way of example and not limitation, a lower limit and/or an upper limit may be selected from 0.5, 1, 1.5, 2, 2.5, 3, 3.5, 4, 4.5, 5, 5.5, 6, 6.5, 7, 7.5, 8, 8.5, 9, 9.5 and 10% by weight. A range formed from a single lower limit includes at least the lower limit and all numerical values greater than the lower limit regardless of whether the values are explicitly recited in this disclosure. A range formed from a single upper limit includes at least the upper limit and all numerical values less than the upper limit regardless of whether the values are explicitly recited in this disclosure. A range formed from a combination of a lower limit and an upper limit includes at least the lower limit, the upper limit, and all numerical values therebetween regardless of whether the values are explicitly recited in this disclosure. For example, based on the set of exemplary upper limits and lower limits explicitly recited above, according to various embodiments, core may contain the metal micronutrient in an amount of: about 0.5 to about 10% by weight, less than about 0.5% by weight, greater than about 0.5% by weight, less than about 10% by weight, or greater than about 10% by weight, etc. All such ranges are contemplated and are intended to be explicitly disclosed and recited. Each value recited is intended to be modified by the term "about." As an example, according to various embodiments, the core may comprise Zn in an amount of from about 1 to about 5% by weight, or in an amount of about about 2.5% by weight (25,000 ppm). Various embodiments include amounts of a metal micronutrient in the core that are non-phytotoxic for the particular plant. For example, up to 1000 ppm of metallic Zn has been tested against ornamental vinca and found to be non-phytotoxic.

An advantage of various embodiments is that the core 102 may eventually degrade to metal ions, which may then be metabolized by the plant, leaving behind no nano-residue in the plant.

Shell of the Cargo Delivery Particle(s)

Still referring to FIG. 1, the shell 103 may be disposed on or around the core 102. The shell 103 may cover or coat all or a portion of an exterior surface of the core 102. One or more cargos 104 may be disposed on the shell 103.

According to various embodiments, the shell may be made of a coating material that may interact with the cargo. According to various embodiments, the interaction between the coating material and the cargo(s) may include a covalent bond, a non-covalent interaction, an intermolecular interaction, or any combination thereof. As used herein, a covalent bond refers to a chemical bond that involves the sharing of electron pairs between atoms. Covalent bonding includes many kinds of interactions, including at least σ-bonding, π-bonding, metal-to-metal bonding, agostic interactions, bent bonds, and three-center two-electron bonds. As used herein, a non-covalent interaction differs from a covalent bond in that it does not involve the sharing of electrons, but rather involves more dispersed variations of electromagnetic interactions between molecules or within a molecule. Non-covalent interactions include at least electrostatic interactions, Van der Waals forces, π-effects, hydrophobic effects. Electrostatic interactions may include at least ionic interactions, hydrogen bonding, and halogen bonding. Van der Waals forces may include at least dipole-dipole interactions, dipole-induced dipole interactions, and London dispersion forces. π-effects may include at least π-π interactions, cation-π interactions, anion-π interactions, and polar-π interactions. As used herein, intermolecular interactions or forces are the forces which mediate interaction between molecules, including forces of attraction or repulsion which act between molecules and other types of neighboring particles, e.g. atoms or ions. Intermolecular interactions include at least ion—dipole interactions, dipole—dipole interactions, dipole—induced dipole interactions, and induced dipole—induced dipole interactions. Any of these types of interactions or any combination of these types of interactions may provide a mechanism by which the coating material may interact with the cargo(s) disposed thereon or associated therewith.

The coating material may be any material suitable for coating the core and providing a desirable interaction with a particular cargo to be delivered. According to various embodiments, the coating material may comprise N-acetylcysteine (NAC), salicylate, caffeine, or any combination thereof. For example, various embodiments provide a composition and a method of making "protein-sized" zinc oxide (ZnO) nanoparticles coated with N-acetylcysteine (NAC). Zinc oxide nanoparticles coated with N-acetylcysteine (NAC-ZnO) is an example of a systemic cargo delivery system according to various embodiments. A wide range of cargos can be systemically delivered using NAC-ZnO, as long as NAC interacts with the cargos of interest. For various applications, the coating material, such as a NAC coating, may be useful to improve dispersibility (solubility) of the core nanoparticles, such as ZnO, in an aqueous medium, as well as, to prevent agglomeration of the nanoparticles. Various tested embodiments demonstrate that NAC-ZnO is capable of systemic delivery of a cargo comprising antimicrobial 2S-albumin protein (~12.5 kDa) to a vascular plant, in particular the phloem of *citrus* plant, for controlling Huanglongbing (aka *citrus* greening).

Embodiments comprising NAC-ZnOAn have the advantage that NAC and Zn are generally recognized as safe (GRAS), requiring minimal regulatory requirements. Both Zn and NAC should be considered favorably by Organic Materials Review Institute (OMRI) for organic farming. In fact, both NAC and Zn are nutritional supplements for humans.

Some Exemplary Cargo(s)

Various embodiments provide systemic delivery of a wide variety of cargos. For convenience and clarity, some examples of various cargos are grouped into categories hereinafter, but it should be understood than any cargo or combination of cargos may be employed. Cargos may include therapeutic molecules for controlling plant disease or any type of plant deficiencies, such as antimicrobial compounds. Cargos may include agrichemical active ingredients, such as insecticides, bactericides, fungicides, or combinations thereof. For example, according to various embodiments, a cargo may comprise mancozeb. Mancozeb is registered as a general use pesticide by the U.S. Environmental Protection Agency. Mancozeb is a dithiocarbamate non-systemic agricultural fungicide with multi-site, protective action on contact. More specifically, mancozeb is a combination of two other dithiocarbamates: maneb and zineb. The mixture controls many fungal diseases in a wide range of field crops, fruits, nuts, vegetables, and ornamentals. Cargos may include metal micronutrients, as described above with respect to possible components of the core. Examples of metal micronutrients include, but are not limited to iron (Fe), copper (Cu), zinc (Zn), manganese (Mn), molybdenum (Mo), nickel (Ni), and various combinations thereof. Cargos may include biomolecules, such as proteins, peptides, nucleic acids, Systemic Acquired Resistance (SAR) chemicals, antioxidants, or combinations thereof. For example, according to various embodiments, a cargo may comprise double-stranded RNA.

According to various embodiments, a cargo may comprise a 2S albumin. 2S albumins are a major class of seed storage proteins, which constitutes a major protein fraction of seed proteins in the Euphorbiaceae (44%) and Cucurbitaceae (56%) families of plants. The low molecular weight seed proteins belonging to 2S albumin storage family are made of two disulfide linked polypeptide chains of around 4 kDa and 10 kDa. They are characterized by the presence of eight conserved cysteines forming four disulfide bridges, two interchain and two intrachain in large subunit. Apart from conserved cysteines, the amino acid sequence homology is relatively low within and among plant species. They exhibit a compact structure made of five $\alpha$-helices stabilized by four conserved disulfide bonds.

2S albumins may be purified and characterized from different plant species. 2S albumins may exhibit different types of biological activities, such as translational inhibitory activity, antibacterial activity, antifungal activity, and serine protease inhibitor activity. Some 2S albumins from different plants are characterized as major food allergens and are able to bind IgE from allergic patients' sera. The 2S albumin characterized from *Putranjiva roxburghii* seeds showed DNase, RNase and antifungal activities.

2S albumins may be purified and characterized from plant seeds of *Cucurbita maxima*. These proteins exhibited multiple functions which may have potential biotechnology applications. The purified 2S albumin from *Cucurbita maxima* (Pumpkin) exhibited anticancer, DNase and antifungal activities. It also showed a strong anti-cancer activity toward breast cancer (MCF-7), ovarian teratocarcinoma (PA-1), prostate cancer (PC-3 and DU-145) and hepatocellular carcinoma (HepG2) cell lines. Acridine orange staining and DNA fragmentation studies indicated that cytotoxic effect of pumpkin 2S albumin is mediated through induction of apoptosis. Pumpkin 2S albumin showed DNase activity against both supercoiled and linear DNA and exerted antifungal activity against *Fusarium oxysporum*. Secondary structure analysis by CD showed that protein is highly stable up to 90° C. and retains its alpha helical structure.

A variety of antimicrobial proteins may be employed to provide good antifungal, antibacterial and serine proteinase activity. For example, 2S albumin protein may be employed to inhibit microbial growth. The SiAMP2, a 2S albumin family protein from *Sesamum indicum* kernels, has been shown as detrimental to *Klebsiella* species.

As discussed in the Example hereinafter, inhibition of *E. coli* (DH5a), a CLas family of gram-negative bacterium, cultured in vitro using media containing varying concentrations of 2S albumin protein, extracted from the seeds of pumpkin (*Cucurbita maxima*). This suggests the possibility of applying 2S albumin protein as one of curative agents against HLB. The pumpkin 2S albumin is heterodimeric (~12.5 kDa in size) seed storage protein that is thermally stable and water-soluble. This protein has demonstrated anticancer, RNase/DNase and antifungal activities. Far-UV (190-260 nm) CD spectroscopy studies for secondary structure showed that the protein is thermally stable up to 90° C., retaining its alpha helical structure.

Methods of Administration

Figure 2:
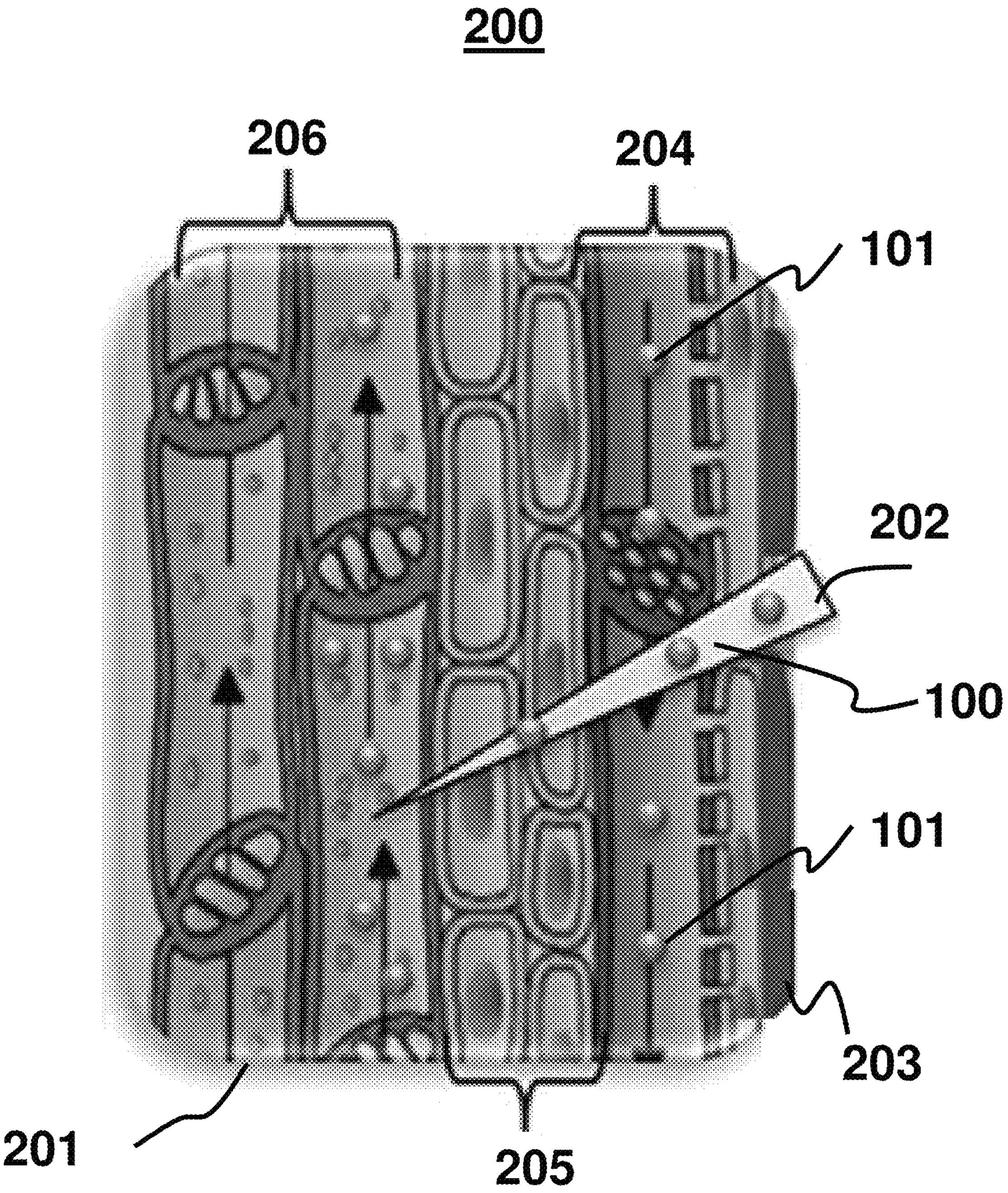
FIG. 2: is an example according to various embodiments illustrating a method of administering a composition to a vascular plant.

FIG. 2 is an example according to various embodiments illustrating a method 200 of administering a composition to a vascular plant 201. The vascular plant 201 may be, for example, a CLas-infected Mosambi plant. A composition 100 comprising at least one cargo delivery particle 101 and at least one cargo (not specifically shown) associated therewith may be injected into the vascular plant 201 via a needle 202. The needle 202 may penetrate the bark 203, the phloem 204, the cambium 205, and into the xylem 206 where the composition 100 may be injected.

The cambium 205 (plural cambia or cambiums) is a tissue layer that provides partially undifferentiated cells for plant growth. It is found in the area between the two types of transport tissue in vascular plants, xylem 206 and phloem 204. Particles having sizes, larger than about 10 nm are often phloem-restricted, having limited accessibility to phloem tissue, although they can populate xylem vasculature easily after their root uptake. Various embodiments provide efficient, systemic delivery of cargos to plant vasculature system, in particular to phloem tissue. As used herein, the term "phloem tissue" or "phloem" has its usual meaning and refers generally to the living tissue in vascular plants that transports the soluble organic compounds made during photosynthesis. In trees, the phloem is the innermost layer of the bark, hence the name, derived from the Greek word φλοιός (phloios) meaning "bark". Particles having sizes larger than 10 nm often have limited accessibility to phloem tissue although they can populate xylem vasculature easily after their root uptake. As used herein, the term "size" as it relates to particles generally refers to an average diameter of a plurality of particles. For particles that are not perfectly spherical, the term "diameter" generally refers to the average of cross-sectional diameters in a plurality of directions such that the "diameter" is a reasonable approximation of the average dimensions of the particles. As such, all specific numerical values associated with particle size as used herein should be understood to be modified by the term "about." For example, a particle having a size larger than 10 nm may generally refer to a particle that would be likely to be captured by a filter having 10 nm gaps. Similarly, a plurality of particles having a size larger than 10 nm would indicate that on average the particles would be likely to be captured by a filter having 10 nm gaps.

Various embodiments provide a systemic cargo delivery system for plants that may also be applied with traditional application methods (foliar, soil-drench), no such cargo delivery system currently exists for treating plants. Various embodiments of the composition may also be useful in seed/fertilizer coatings.

Methods of Producing the Composition(s)

Various embodiments provided a straight-forward one-pot synthesis process that can be easily scaled-up. For example, a method of producing the compositions may include dispersing a salt of a metal micronutrient, such as zinc nitrate in a solution with a coating material, such as N-acetylcysteine. The coating material may form a complex by chelating the metal ions. The pH of the solution may then be raised to prompt formation of the cargo delivery particles comprising the metal micronutrient coated with the coating material. Subsequently the cargo may be added to the solution and may interact with the shells of the cargo delivery particles. Various embodiments of the production method are very cost-effective as agricultural-grade metal micronutrients like zinc and food-grade coating materials like N-acetylcysteine may be easily sourced as commodity products.

FIG. 3A is an example according to various embodiments illustrating a method 300 for producing cargo delivery particles according to various embodiments. The method 300 may include a step 302 of dispersing or dissolving a salt of a micronutrient in a solution. Step 302 may include agitating or stirring the solution. The micronutrient may be any micronutrient as described or implied herein, for example the micronutrient may be a metal micronutrient. For example, the salt may be a zinc nitrate, e.g. zinc nitrate hexahydrate, in which case the metal micronutrient would be zinc. The solution may comprise any suitable solvent, such as for example de-ionized (DI) water. After dispersal in the solution, ions of the micronutrient may be present in the solution. For example, zinc ions may be present in the solution. The method 300 may further include a step 304 of adding a coating material to the solution. The coating material may be any coating material as described or implied herein. The method 300 may further include a step 306 of allowing the coating material to interact the ions of the micronutrient. According to various embodiments, the interaction between the coating material and the ions of the micronutrient may be chelation. Chelation is a type of bonding of ions and molecules to metal ions. For example, the coating material may chelate a metal micronutrient. The method 300 may further include a step 308 of raising the pH of the solution. For example, the pH of the solution may be raised by the addition of a base, such as sodium hydroxide. The method 300 may further include a step 310 of allowing the formation of cargo delivery particles, such as the cargo delivery particles 101 illustrated in FIG. 1. The cargo delivery particles may have a core and a shell. The core may comprise the micronutrient and the shell may comprise the coating material. The method 300 may further include a step 312 of purifying the cargo delivery particles. Excess coating material and/or other impurities present in the solution may be removed by dialysis. Dialysis may be carried out for any suitable length of time, for example for a time in a range of from 12 to 72 hours. The solvent, such as DI water, may be changed or refreshed periodically throughout the dialysis period, such as at an interval of about every 8 hours. Finally, the method 300 may include a step 314 of drying the cargo delivery particles. The drying may be any type of drying, such as for example, freeze-drying the entire dialyzed solution. Upon drying, the cargo delivery particles may be obtained in the form of a powder.

Figure 3B:
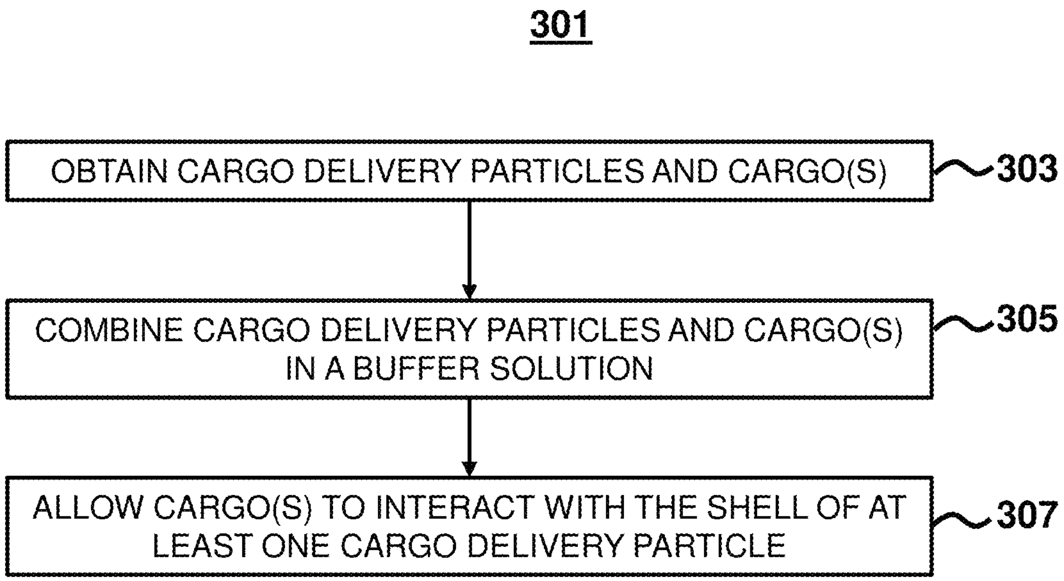
FIG. 3B: is an example according to various embodiments illustrating a method for producing compositions according to various embodiments.

FIG. 3B is an example according to various embodiments illustrating a method 301 for producing compositions according to various embodiments. The method 301 may include a step 303 of obtaining cargo delivery particles and cargo(s). The cargo delivery particles may be obtained, for example, according to a method 300 as illustrated in FIG. 3A. The cargo(s) may be any of the cargos described or implied herein. The cargo(s) may be obtained from a commercial source or may be derived. The example provided hereinafter demonstrates a method of deriving 2S albumin. The method 301 may further include a step of combining the cargo delivery particles and the cargo(s) with a buffer solution. As used herein, a "buffer solution" is an aqueous solution consisting of a mixture of a weak acid and its conjugate base, or vice versa. The pH of a buffer solution changes very little when a small amount of strong acid or base is added. Buffer solutions are used as a means of keeping pH at a nearly constant value according to various embodiments. According to various embodiments, the buffer solution may be phosphate-buffered saline (PBS). The method 301 may further include a step 307 of allowing the one or more cargos to interact with the shell of at least one cargo delivery particle. The cargos may, of course, interact with a plurality of shells. The interaction may be any interaction between a cargo and a shell as described or implied herein.

EXAMPLE

Introduction

The following example is put forth to provide those of ordinary skill in the art with a complete disclosure and description of how to perform the methods and how to make and to use the compositions and compounds disclosed and claimed herein. Efforts have been made to ensure accuracy with respect to numbers (e.g., amounts, temperature, etc.), but some errors and deviations should be accounted for. The purpose of this example is not to limit the scope of the various embodiments, but merely to provide an example illustrating specific embodiments of the composition, the method of making the composition, and the method of administering the composition.

With the objective of developing effective antimicrobials against CLas, an evaluation was made of the antimicrobial efficacy of various trunk-injectable formulations. A first formulation comprised 2S albumin protein isolated from *Cucurbita maxima*. A second formulation comprised cargo delivery particles having a core comprising zinc oxide and a shell comprising N-acetylcysteine; for convenience such cargo delivery particles shall be referred to in this example as "Nano-ZnO." A third formulation comprised a cargo of 2S albumin protein isolated from *Cucurbita maxima* disposed on "Nano-ZnO" cargo delivery particles having a core comprising zinc oxide and a shell comprising N-acetylcysteine. Growth of CLas bacterium (measured as changes in its titer) in infected 3-year-old Mosambi plants (*Citrus sinensis*) grafted on rough lemon (*C. jambhiri*) root stock was monitored after treatment to determine HLB killing efficacy.

The following examples demonstrate for the first time an in planta efficacy of two antimicrobial compounds against CLas viz. 2S albumin (a plant-based protein; ~12.5 kDa), Nano-Zinc Oxide (Nano-ZnO; ~4.0 nm diameter) and their combinations. Aqueous formulations of these compounds were trunk-injected to HLB affected Mosambi plants (*Citrus sinensis*) grafted on 3-year old rough lemon (*C. jambhiri*) rootstock with known CLas titer maintained inside an insect-free screen house. The effective concentration of 2S albumin (330 ppm) coupled with the Nano-ZnO (330 ppm) at 1:1 ratio was used.

The dynamics of CLas pathogen load of treated Mosambi plants was assessed using TaqMan-qPCR assay every 30 days after treatment (DAT) and monitored till 120 days. It was observed that 2S albumin-Nano-ZnO formulation performed the best among all the treatments decreasing CLas population by 96.2%, 97.6%, 95.6%, and 97% of the initial bacterial load (per 12.5 ng of genomic DNA) at 30, 60, 90, and 120 DAT, respectively. These examples demonstrate the potency of 2S albumin-Nano-ZnO formulation as an antimicrobial treatment for suppressing CLas in planta. The results further demonstrate that the compositions and methods according to various embodiments may be employed as anti-CLas therapeutics to mitigate the HLB severity affecting the *citrus* industry worldwide.

Production of HLB-Positive Experimental Plants

Figure 4A:
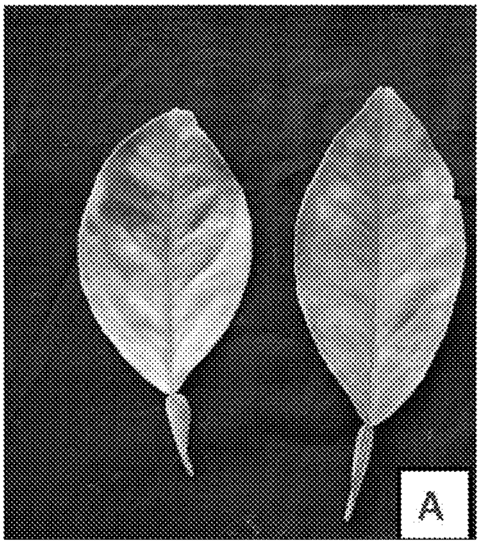
FIG. 4A: is an example according to various embodiments illustrating a photograph of HLB symptoms of blotchy mottle on leaves of Mosambi (*Citrus sinensis*)
Figure 4B:
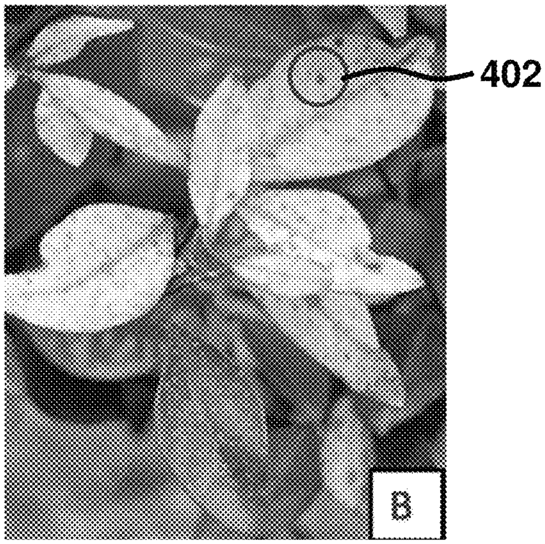
FIG. 4B: is an example according to various embodiments illustrating a photograph of HLB symptoms of blotchy mottle and green island symptoms on leaves of Mosambi (*Citrus sinensis*)
Figure 4C:
FIG. 4C: is an example according to various embodiments illustrating a photograph of experimental HLB affected Mosambi plants.

Healthy two-year-old Mosambi plants grafted on rough lemon rootstock were raised inside an insect-free screen house at ICAR-Central *Citrus* Research Institute, Nagpur, India. These plants were graft-inoculated with CLas-affected Mosambi scions and subsequently maintained in the screen house at temperatures ranging from 32±5° C. (daytime) to 22±5° C. (night) during the entire period of the experiment. The plants showing typical HLB symptoms of blotchy mottle and vein corking on leaves after 3-5 months of graft inoculation (See: FIGS. 4A and 4B) were tested for CLas by conventional PCR using CLas specific primers (OI1/OI2c) and PCR positive plants were selected for further investigations. Total of eighteen CLas positive and three healthy plants (See: FIG. 4C) were selected based on positive conventional PCR. qPCR was performed for each of the experimental plants to determine the Ct values before and after the treatments as outlined below.

FIGS. 4A, 4B, and 4C show HLB disease symptoms on Mosambi (*Citrus sinensis*). More specifically, FIG. 4A is an example according to various embodiments illustrating a photograph of HLB symptoms of blotchy mottle on leaves of Mosambi (*Citrus sinensis*). FIG. 4B is an example according to various embodiments illustrating a photograph of HLB symptoms of blotchy mottle and green island symptoms on leaves of Mosambi (*Citrus sinensis*). Circled portion 402 is an example of green island symptoms. FIG. 4C is an example according to various embodiments illustrating a photograph of experimental HLB affected Mosambi plants.

Designing Primers, Probe and TaqMan-qPCR Assay Conditions

The CLas specific primer pair (HLBas-F/-Rn) and probe (HLBp) based on sequences of 16S rDNA with an expected amplicons length of 76 bp (GenBank accession number L22532) were custom synthesized from Integrated DNA Technologies (Coralville, Iowa, USA). HLBp (probe) was labeled at the 5' terminal end with 6-carboxy-fluorescein (FAM) reporter dye and 3' terminal end nucleotide with Black Hole Quencher (BHQ)-1dye (See: Table 1). This probe was used for standardization of TaqMan assay. An additional primer-probe set was synthesized on the basis of the sequence (GenBank accession number CX297817) of plant cytochrome oxidase (COX). The COX probe (COXp) was labelled with JOEN reporter dye with BHQ-2 at the 3' terminal end and used as a positive internal control to assess the quality of DNA in reaction cocktails. The real-time PCR assay was performed using a Real Time PCR System (Applied Biosystems) in a total of 20 μl reaction volume consisting of the following reagents at the optimized concentrations: 300 nM (each) target primers (HLBas-F/HLBas-Rn), 200 nM target probe (HLBp), 300 nM (each) internal control primers (COXf and COXr), 200 nM internal control probe (COXp) with 1× TaqMan Universal Master Mix II (Applied Biosystems). The protocol was 95° C. for 10 min, followed by 40 cycles at 95° C. for 20 s, 58° C. for 30 s and 60° C. for 30 s. All reactions were performed in triplicate along with non-template controls. Table 1 provides a list of primer and probe sets used for qPCR assay.

Specificity and Sensitivity of TaqMan-qPCR Assay

The specificity and sensitivity of the HLBas-F/Rn primers towards the target were evaluated. The sensitivity of assay and analysis of data were performed by StepOne Software v2.1 (Applied Biosystems). Standard curve and amplification efficiency were determined by use of 1:10 serially diluted genomic DNA (12.5 ng, 1.25 ng, 0.125 ng, 0.0125 ng, 1.25 μg, 0.125 μg and 12.5 fg) from CLas infected Mosambi plants.

The Synthesis of N-Acetyl-L-Cysteine (NAC) Coated Nano-ZnO

The NAC coated Nano-ZnO was prepared using a wet chemical synthesis process. Zinc nitrate hexahydrate (1488 mg) ($Zn(NO_3)_2.6H_2O$; Sigma-Aldrich; catalogue #228737) was dissolved in 20 ml de-ionized (DI) water. Subsequently, 408 mg of NAC powder (Sigma-Aldrich; catalogue #A7250) was added and stirred until NAC was completely dissolved. Finally, the pH was adjusted to 9.0 with 1M NaOH.

Purification of NAC Coated Nano-ZnO

Excess NAC and other impurities present in the solution containing NAC coated Nano-ZnO product was removed by dialysis (Spectrum Labs, Spectra/Por 3 standard RC dry dialysis tubing, MWCO 3.5 kD). Dialysis was carried out for 72 hours changing DI water in every 8 hours. Nearly 300 mg of purified NAC coated Nano-ZnO powder was obtained after freeze-drying the entire dialyzed (initial volume of 25 ml) solution. Hereafter, the NAC coated Nano-ZnO was abbreviated as Nano-ZnO.

Nano-ZnO Characterization

High-resolution Transmission Electron Microscopy (HR-TEM) was used to characterize particle size and crystalline phase of Nano-ZnO in vacuum state. Particle size and surface charge in solution were determined by Dynamic Light Scattering (DLS) using Malvern Zetasizer (model Nano ZS90).

Determination of Metallic Zinc Content of Nano-ZnO Powder

Atomic Absorption Spectroscopy (AAS; Perkin Elmar Analyst 400) was used to determine Zn content in Nano-ZnO. AAS sampling performed using 5 replicates for this study. In a 50 ml disposable centrifuge tube (VWR; Catalogue #89039-658), 20 mg of Nano-ZnO powder was added to 20 ml of 1% HCl solution. The tubes were placed in a mechanical shaker for 12 hours to digest the particles. The resulting solution was clear and the pH was approximately 1.8 and showed no characteristic UV-Vis or fluorescence

TABLE 1

| Target gene | Primer/ Probe Code | Primer/ Probe Sequence (5'-3') | Concen-tration (nM) | Amplicon Size (bp) |
|---|---|---|---|---|
| 16S r DNA of *Candiadatus Liberibacter asiaticus* | HLBas-F | TCGSGCGCGTSTGCSSTCG (SEQ ID NO: 1) | 25 | 76 |
| | HLBas-Rn | GCGTTATCCCGTAGAAAAAGGTAG (SEQ ID NO: 2) | 25 | |
| | HLBp | 56-FAM/AGACGGGTGAGTAACGCG/ 3BHQ_1 (SEQ ID NO: 3) | 250 | |
| Plant cytochrome oxidase | COX-F | GTATGCCACGTCGATTCCAGA (SEQ ID NO: 4) | 25 | 68 |
| | COX-Rn | GCCAAAACTGCTAAGGGCATTC (SEQ ID NO: 5) | 25 | |
| | COXp | 56-JOEN/ATCCAGATGCTTACGCTGG/ 3BHQ_2 (SEQ ID NO: 6) | 250 | |

peaks, confirming complete digestion of Nano-ZnO. Metallic Zn content was determined to be about 53% (wt/wt).

Phytotoxicity Assessment of Nano-ZnO

Plant tissue damage potential (phytotoxicity) of Nano-ZnO and zinc nitrate were tested against ornamental vinca (vincire) plants (obtained from local Home Depot store) at 72 hours post foliar application. Ornamental vinca plants are susceptible to metal phytotoxicity such as Cu and used as industry standard. 3 plants were foliar sprayed with each treatments and controls at three different rates, 300 ppm, 600 ppm and 1,000 ppm. Test solutions were foliar applied using hand-operated pump mist sprayer till run off. Afterwards, plants were placed in plant growth chamber (Panasonic MLR-325H-PA) programmed to simulate summer conditions (maximum temperature set at 31° C.). Visual observations were conducted after 72 hours application to assess the overall plant health and phytotoxicity rating.

Preparation of 2S Albumin Protein and Nano-ZnO Formulation 2S albumin protein was isolated and purified as described earlier with some modifications from the seeds of pumpkin (*Cucurbita maxima*) and the effective antimicrobial concentration was determined based on in vitro experimental data against *E. coli* (DH5a). Briefly, the pumpkin seeds were ground and soaked overnight in 50 mM of Tris-HCl. The extract was filtered and centrifuged at 18000 rpm for 60 min. The supernatant was passed through a pre-equilibrated DEAE-Sepharose column (1.5×10 cm) and the flow through was applied on to a CM-Sepharose column (1.5×8 cm) pre-equilibrated with 50 mM Tris-HCl buffer, pH 7.4. The bound proteins were eluted with a step gradient of NaCl in same buffer (50, 100, 300 and 500 mM). The fraction (eluted at 300 mM NaCl) was applied onto a gel-exclusion chromatography column (Superdex 75, 10/300 GL) pre-equilibrated with 50 mM Tris-HCl buffer, pH 7.4. The purity of the eluted protein was confirmed by a single band on a non-reducing 12% SDS-PAGE. The purified protein was concentrated to 0.33 mg/ml and used in further experiments.

Trunk Injection of 2S Albumin Protein, Nano-ZnO and Zinc Nitrate

HLB infected, and healthy Mosambi plants with stem diameter of ~1.5 cm were injected with 2S albumin protein, Nano-ZnO and Zinc nitrate in five different combinations. A hole 2-3 mm diameter, and 6-8 mm depth was drilled on the trunk using a Kangaroo professional 10/13 MM IMPACT DRILL (Model No: KID 10/13 USA) with 2 mm bit. The drilled holes on trunk were 6 to 8 cm from the soil surface and at a 45° angle downward direction to avoid leakage of solution during trunk injection. The hole was drilled in such a manner that the end point of the bit would reach phloem and xylem region. The bits were surface wiped with 70% ethanol before and after use to prevent any secondary infection. Five different treatments were carried out: a) 2S albumin protein (330 ppm), b) Nano-ZnO (1,000 ppm), c) 2S albumin (330 ppm) plus Nano-ZnO (330 ppm), d) 2S albumin protein (330 ppm) plus Zinc nitrate (165 ppm) and e) Zinc nitrate (165 ppm). Each treatment had three replicates. Zn concentrations were carefully selected to minimize any potential phytotoxicity and residual effects. Preliminary phytotoxicity assessment was carried out against vinca model plants via foliar spray application, and it was found that Nano-ZnO was not phytotoxic up to 1,000 ppm (μg/mL). Zinc nitrate was found to be moderately phytotoxic even at 600 (μg/mL) and non-phytotoxic at 300 (μg/mL) (See: Table 4). It was expected that the soluble form of Zn (such as Zn nitrate) would be at higher risk of causing phytotoxicity than ZnO if it is trunk-injected at elevated concentration (e.g. 1,000 ppm metallic Zn). Three HLB infected drilled plants were taken as positive control (without any treatment) and three HLB-free plants were kept as negative control (healthy control). we used 330 ppm solution each of Nano-ZnO and 2S albumin protein individually in 10 mM PBS buffer (pH7.4). Desired amount of Nano-ZnO lyophilized powder was dissolved in PBS (pH 7.4), vortexed for 2 min and sonicated with Q SONICA sonicator (Ultrasonic Processor) for 5 min in glass vials. The prepared 2S albumin protein solution in PBS buffer was mixed in a 1:1 ratio with the Nano-ZnO solution and sonicated for 60 min. The plants having similar initial bacterial load were treated as outline above, for four months at monthly intervals from November 2016 to March 2017. The injected volume was 50 μl each day for three consecutive days of every month during morning hours. The holes were sealed with parafilm after injection to avoid leakage and opportunistic contamination. Same holes were re-drilled timely for subsequent timely injections.

DNA Extraction and Evaluation of CLas Load using TaqMan-qPCR Assay

The experimental plant was injected with different combinations of treatment viz, a) 2S albumin protein, b) Nano-ZnO, c) 2S albumin plus Nano-ZnO, d) 2S albumin protein plus Zinc nitrate and e) Zinc nitrate and assayed over a period of four months. The CLas titer was determined in control and treated plants every 30 days. The collected leaves were washed with sterile water, wiped with 70% ethanol to avoid surface contamination and blot dried. Midribs and petioles were excised and ground in liquid nitrogen. And 100 mg of the sample was used for DNA extraction using the DNeasy Plant mini kit (Qiagen, Hilden, Germany) as per the manufacturer's protocol.

Monitoring of CLas Titer in Treated and Control Plants

The effectiveness of 2S albumin protein and Nano-ZnO against CLas load was analyzed by monitoring the titer of CLas using qPCR with TaqMan chemistry after every treatment before the first injection (0), and 30, 60, 90, 120 DAT. All treatments were performed in triplicate using negative controls (template from untreated healthy plant), positive controls (template from untreated HLB affected plant) and non-template controls. The data were analyzed using StepOne Software v2.1.

Quantification of CLas Genome Copy Number in Experimental Plants and Data Analysis The quantification of CLas copy number was carried out using the standard curve method to determine the effectiveness of treatment. The fragment of 16S rDNA from CLas was amplified with the HLBas-F and HLBDr-3 primers pair (See: Table 2). The amplified PCR product (432 bp) was cloned into the T-Vector pMD20 from Integrated DNA Technologies (Coralville, Iowa, USA). The cloned fragment was used as template for titer determination to generate the standard curve. The 10-fold serial dilutions in nuclease-free water were used (5.5 ng of initial template DNA up to $10^{-9}$). The initial concentration of the template DNA was estimated using Thermo Scientific NanoDrop™ 2000 Spectrophotometer. The standard curve was prepared with obtained Ct values using serially diluted template DNA by StepOne Software v2.1. The standard linear regression equation was obtained. The template DNA copy number was calculated with the help of following formula: Number of copies=(amount of target DNA in nano grams)×Avogadro's number ($6.0221\times10^{23}$)/length of DNA amplicon in base pair (bp)×$660\times1\times10^{9}$. Finally, CLas copy number (per 12.5 ng of total genomic DNA) at 0, 30, 60, 90 and 120 DAT was calculated by extrapolating with the standard curve. An equal quantity of DNA was used for the determination of CLas copy number after every month. Additionally, COX gene was used as internal control for normalization of the target gene. Table 2 is a list of primer set used for PCR product cloning.

TABLE 2

| Target gene | Primer Code | Primer Sequence (5'-3') | Concen-tration | Amplicon size (bp) |
|---|---|---|---|---|
| 16S r DNA of *Candiadatus* | HLBas-F | TCGAGCGCGTATGCAATACG (SEQ ID NO: 7) | 25 nM | 432 |
| *Liberibacter asiaticus* | HLB-Dr3 | CTCGCCCCCTTCGTATTACC (SEQ ID NO: 8) | 25 nM | |

During evaluation of effectiveness of different treatments, the final genome copy number of CLas was calculated by subtracting the genome copy number at 30, 60, 90 and 120 DAT from initial genome copy number (at 0 days of treatment). The fold-change in CLas genome copy number was determined by dividing the average of total pathogen titer before the treatment by the total titer of each at 30 DAT. The effect of each treatment on CLas titre at different intervals were analyzed using Graph Pad Software. Significance differences were determined using two-sided paired t-test at a 95% confidence level. Statistical analysis revealed that variations in the CLas titre before and after treatment were significant ($P<0.05$).

Results

Efficiency and Sensitivity of TaqMan-qPCR

Figure 5A:
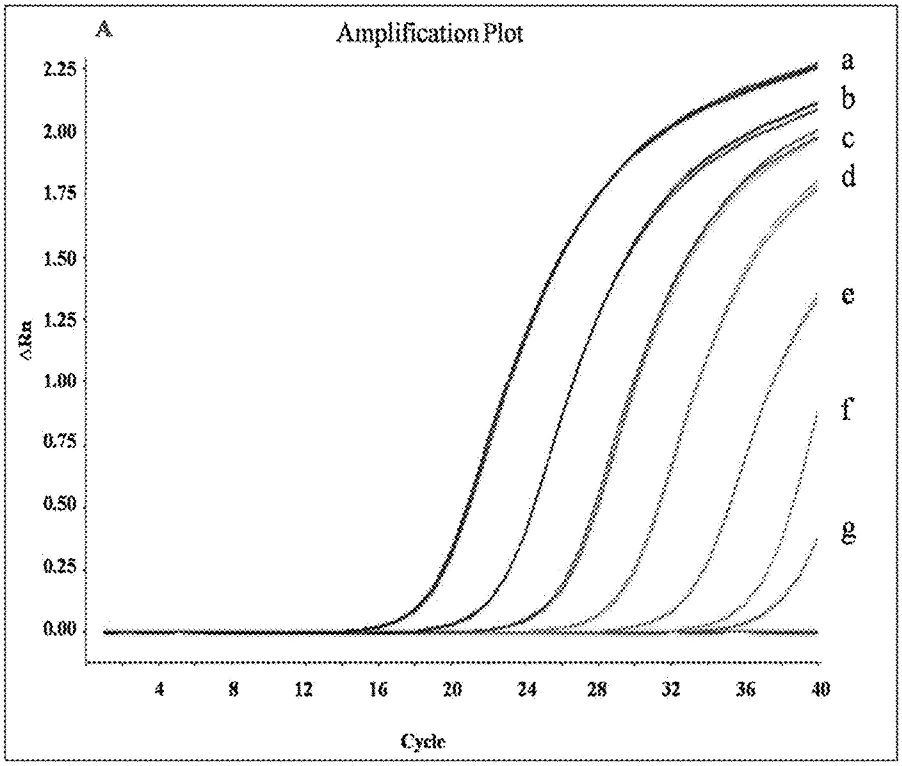
FIG. 5A: is an example according to various embodiments illustrating shows qPCR Amplification plot generated by known concentration of CLas genomic DNA to check efficiency and sensitivity of TaqMan-qPCR with HLBas-F/Rn-HLBp primer probe pair.
Figure 5B:
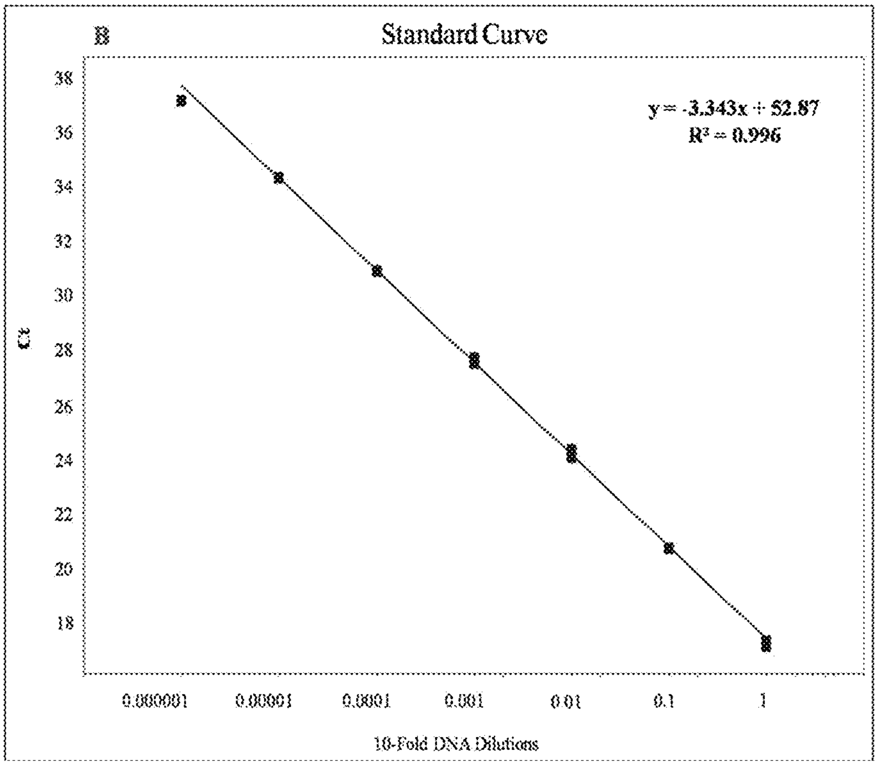
FIG. 5B: is an example according to various embodiments illustrating shows sensitivity of the primer-probe combination (HLBas-F/Rn-HLBp specific) for CLas detection using TaqMan qPCR assay.

The standardized TaqMan-qPCR assay consistently detected CLas in infected Mosambi plants and extracted DNA at concentrations ranging from 0.0125 µg to $12.5\times10^3$ µg (FIG. 5A). The assay showed standard fluorescence with exponential amplification of PCR amplicon and the standard curve was generated (FIG. 5B). The association between Ct value and DNA quantities were robust with correlation coefficient ($R^2$) of 0.996 for HLBas-F/Rn-P and 0.999 for COX-F/R-P (the latter used as internal control). The pathogen detection limit of standardized qPCR assay was 0.0125 pg of total DNA from HLB infected plant. Despite uneven distribution of CLas bacteria, abundant amount of CLas (low Ct value) was detected after standardization of the protocols viz., the annealing temperature and extension time. Thus, the TaqMan-qPCR assay was used subsequently to test the CLas load, before and after the application of antimicrobial 2S albumin protein and Nano-ZnO either individually or in combination.

FIG. 5A is an example according to various embodiments illustrating qPCR Amplification plot generated by known concentration of CLas genomic DNA to check efficiency and sensitivity of TaqMan-qPCR with HLBas-F/Rn-HLBp primer probe pair, Line-a=12.5 ng, Line-b=1.25 ng, Line-c=0.125 ng, Line-d=0.0125 ng, Line-e=1.25 pg, Line-f=0.125 µg and Line-g=12.5 fg template DNA. FIG. 5B is an example according to various embodiments illustrating shows sensitivity of the primer-probe combination (HLBas-F/Rn-HLBp specific) for CLas detection using TaqMan qPCR assay. The standard curve established between log of DNA concentrations vs. cycle threshold (Ct) obtained using 10-fold serial dilution of total genomic DNA of Mosambi plants infected with CLas (initial concentration 12.5 ng/µl, final concentration 12.5 fg/µl).

The Quantification of CLas Genome Copy Number in Plant Tissues

Figure 6A:
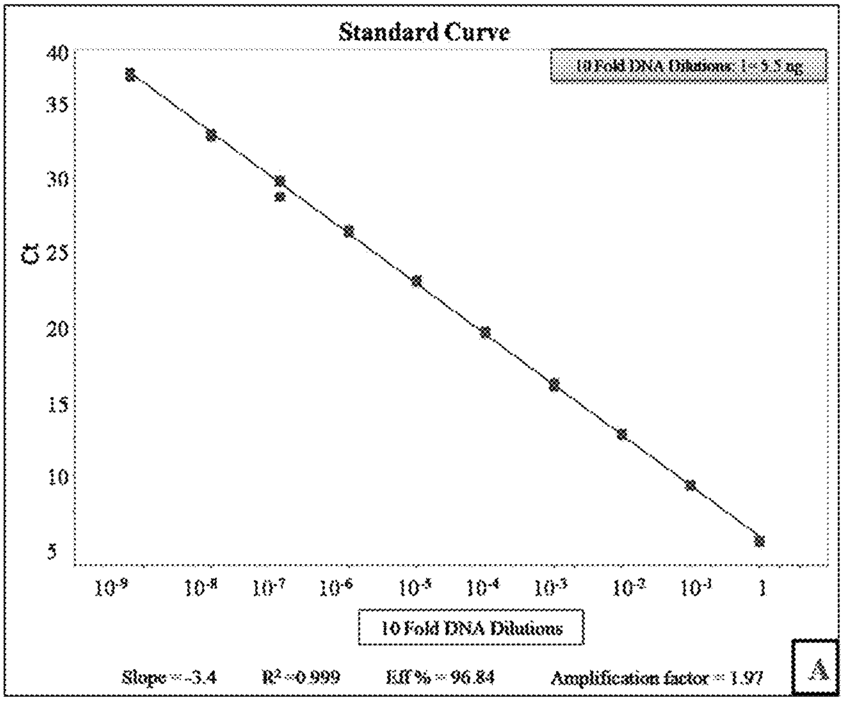
FIG. 6A: is an example according to various embodiments illustrating the quantification of CLas genome copy number with standard curve.
Figure 6B:
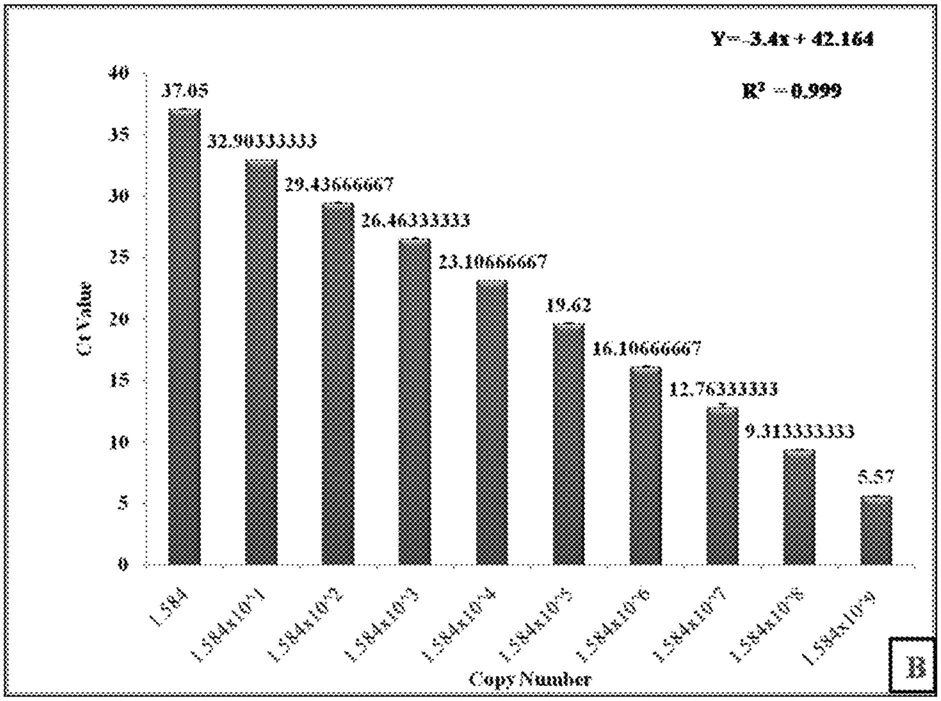
FIG. 6B: is an example according to various embodiments illustrating the exponential relationship between copy number and Ct (Cycle Threshold) value.

FIG. 6A is an example according to various embodiments illustrating the quantification of CLas genome copy number with standard curve. FIG. 6B is an example according to various embodiments illustrating the exponential relationship between copy number and Ct (Cycle Threshold) value. The TaqMan-qPCR reactions were performed with known copy number and 10-fold serially diluted template DNA to determine exact relationship between Ct value and DNA copy number. The initial known template DNA concentration of 5.5 ng per reaction with copy number $1.584\times10^9$ showed an average Ct value of 5.57. The exponential amplification of target amplicon was by at least 3.4 orders of magnitude (FIG. 6A). The exponential relationship between DNA copy number and Ct value was also determined (FIG. 6B). The quantification of CLas genome copy number after each treatment was done with the help of regression equation $Y=-3.4x+42.164$ obtained from standard curve with regression coefficient $R^2=0.99$ and Eff %=96.9. The plant was considered as negative with CLas if the observed Ct value was >36 and was confirmed using HLB specific primers 3F/4R and OI1/OI2c.

The Effectiveness of 2S Albumin Protein and Nano-ZnO Against CLas

All HLB affected Mosambi plants were analyzed for CLas titer individually after every treatment. The results showed a significant difference in CLas titer in control and treated plants with each treatment except Zinc nitrate alone (details given below). A substantial reduction in the CLas genome copy number was observed 30 (DAT) with each treatment administered individually. The CLas titer was also reduced after 60, 90, 120 DAT, but the extent of reduction in CLas genome copy number was low 60 DAT.

Effect of 2S Albumin Protein and Zinc Nitrate on CLas

FIG. 7 shows the CLas titer of infected Mosambi seedling before and at 30, 60, 90, 120 DAT of (A) 2S albumin Protein, (B) 2S albumin Protein plus Zinc nitrate, (C) Nano-ZnO and (D) Zinc nitrate compared with untreated positive control (red color bars indicates infected positive control without treatment whereas blue bars represent treated plants).

Figure 7A:
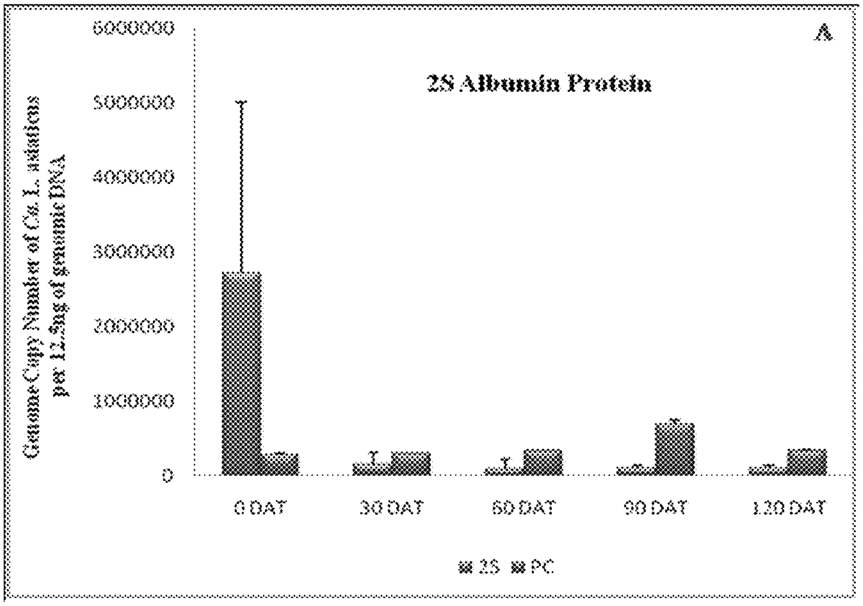
FIG. 7A: is an example according to various embodiments illustrating the CLas titer of infected Mosambi seedling before and at 30, 60, 90, 120 DAT of 2S albumin Protein.

The plants (HLB positive) treated with PBS buffered 2S albumin protein were evaluated by TaqMan-qPCR for CLas titer every 30 DAT (FIG. 7A). Prior to the treatment with 2S albumin protein, the estimated genome copy number of CLas in the plant was $2.72\times10^6$/12.5 ng of genomic DNA with Ct value 19.6, but after 30 DAT the mean Ct value increased to 23.91, indicating the decrease in the pathogen titer from $2.72\times10^6$/12.5 ng of genomic DNA to $1.55\times10^5$. This means that 30 DAT, the genome copy number of CLas decreased by $2.5\times10^6$. In other words, there is 17.47-fold decrement of CLas population in infected Mosambi plants 30 DAT (Table 1). Similarly, CLas load was also monitored 60, 90, 120 DAT. The CLas genome copy number was decreased from $2.72\times10^6$/12.5 ng of genomic DNA to $9.15\times10^4$, $9.9\times10^4$, $9.5\times10^4$/12.5 ng of genomic DNA, respectively (FIG. 7A). Overall, the estimated CLas population/titer is reduced by 17.47, 29.72, 27.44 and 28.56-fold after 30, 60, 90, and 120 DAT, respectively (Table 1). Zinc nitrate treatment alone did not have any effect on CLas titer (FIG.

Figure 7B:
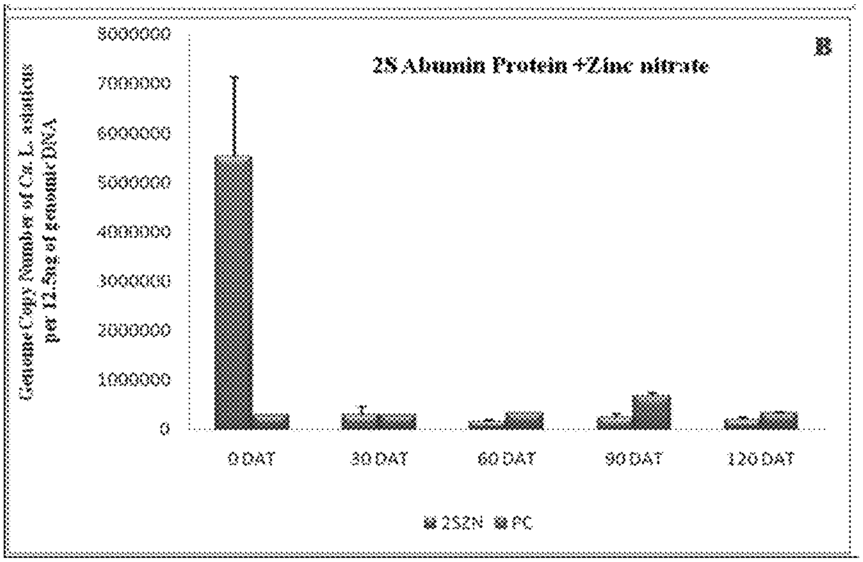
FIG. 7B: is an example according to various embodiments illustrating the CLas titer of infected Mosambi seedling before and at 30, 60, 90, 120 DAT of 2S albumin Protein plus Zinc nitrate.

7D). Further, Zinc nitrate even when applied together with 2S albumin did not show any additive effect in reducing CLas titer (FIG. 7B). This indicates that overall effect of 2S albumin protein either singly or coupled with Zinc nitrate was attributed to the 2S albumin protein alone.

Effect of Nano-ZnO on CLas

Figure 7C:
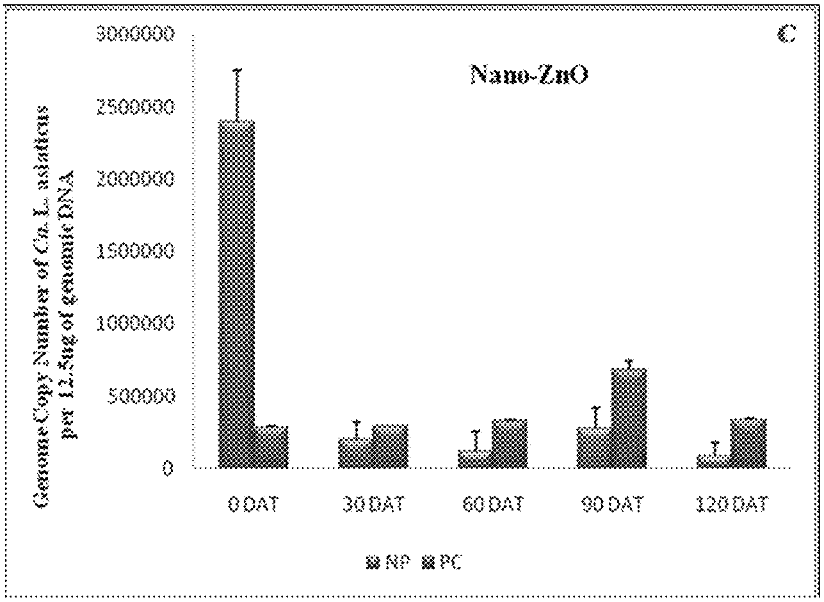
FIG. 7C: is an example according to various embodiments illustrating the CLas titer of infected Mosambi seedling before and at 30, 60, 90, 120 DAT of Nano-ZnO.
Figure 7D:
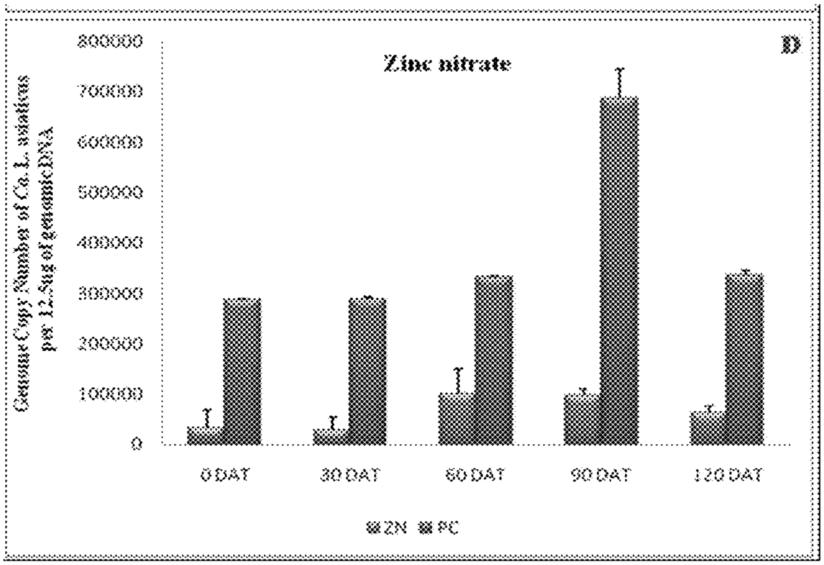
FIG. 7D: is an example according to various embodiments illustrating the CLas titer of infected Mosambi seedling before and at 30, 60, 90, 120 DAT of Zinc nitrate compared with untreated positive control.

Similar to 2S albumin protein, HLB affected plants were treated with Nano-ZnO (1,000 ppm) individually for evaluation of CLas titer every 30 DAT (FIG. 7C). The effectiveness of Nano-ZnO was observed as parallel to the effects recorded with 2S albumin protein. Prior to treatment with Nano-ZnO, the average genome copy number of CLas was $2.3\times10^6$/12.5 ng of genomic DNA with a Ct value 19.8, but 30 DAT the average Ct value increased to 23.5, indicating the decrease of pathogen titer from $2.3\times10^6$/12.5 ng of genomic DNA to $2\times10^5$. This means that 30 DAT with Nano-ZnO, the genome copy number of CLas decreased by $2.1\times10^6$. This is 11.65-fold decrement of CLas titre in Mosambi plants 30 DAT. Similarly, the genome copy number was decreased by 19.56, 8.59, 26.72-fold when checked 60, 90, 120 DAT respectively (Table 3).

Table 3 shows comparative effectiveness of 2S albumin protein and Nano-ZnO on growth and multiplication of CLas in planta.

TABLE 3

| DAT(Days after treatment) | Treatment and fold decrease: 2S albumin | Nano-ZnO | 2S albumin + Nano-ZnO | 2S albumin + Zinc nitrate | Zinc nitrate | No treatment: Positive control |
|---|---|---|---|---|---|---|
| 30 | 17.47 | 11.65 | 27 | 18 | 1 | 1 |
| 60 | 29.72 | 19.56 | 41.69 | 33 | 0 | 0.8 |
| 90 | 27.44 | 8.59 | 23 | 23 | 0 | 0 |
| 120 | 28.56 | 26.72 | 34.16 | 28.18 | 0.5 | 0.8 |

Note:
Negative value in fold change in Zinc nitrate treatment is due to increase in pathogen copy number. (The fold-change was determined by dividing the average of total pathogen titer before the treatment by the total titer of each at 30 DAT).

Effect of 2S Albumin Plus Nano-ZnO

Figure 8:
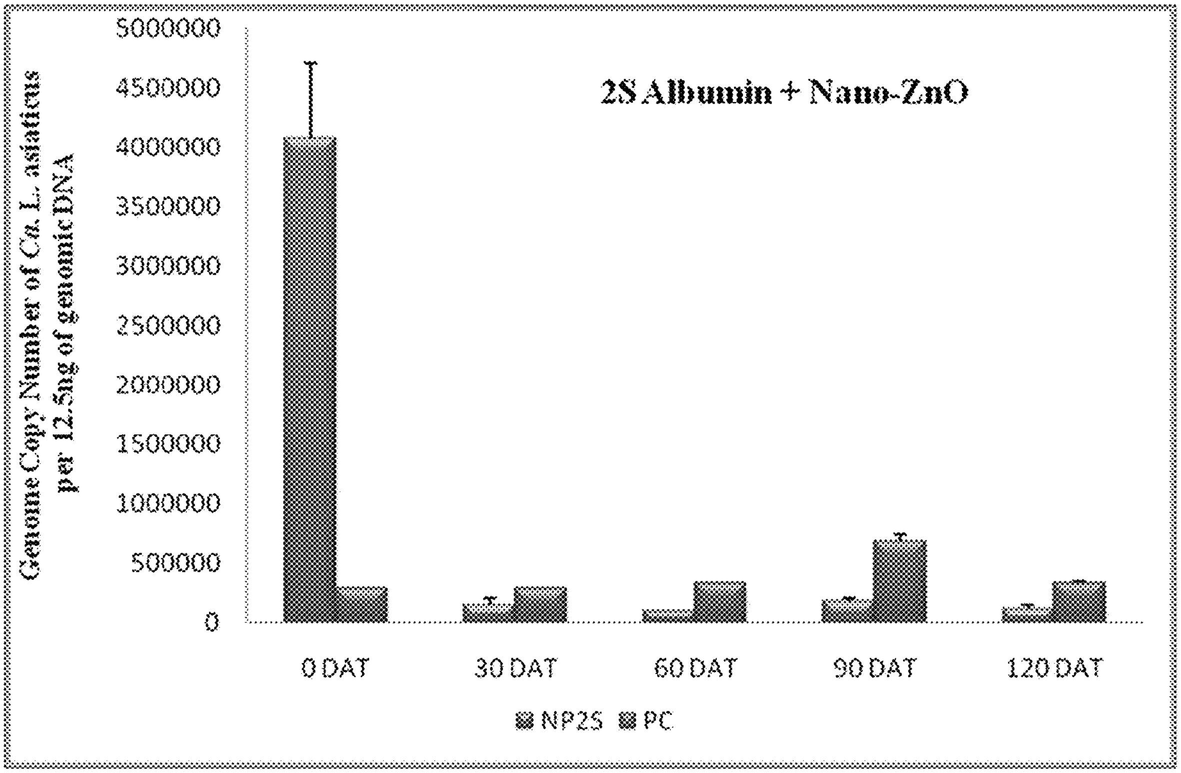
FIG. 8: is an example according to various embodiments illustrating the CLas titer of infected Mosambi plants before the treatment and at 30, 60, 90, 120 DAT with 2S albumin proteins plus Nano-ZnO compared with control plants.
Figure 9:
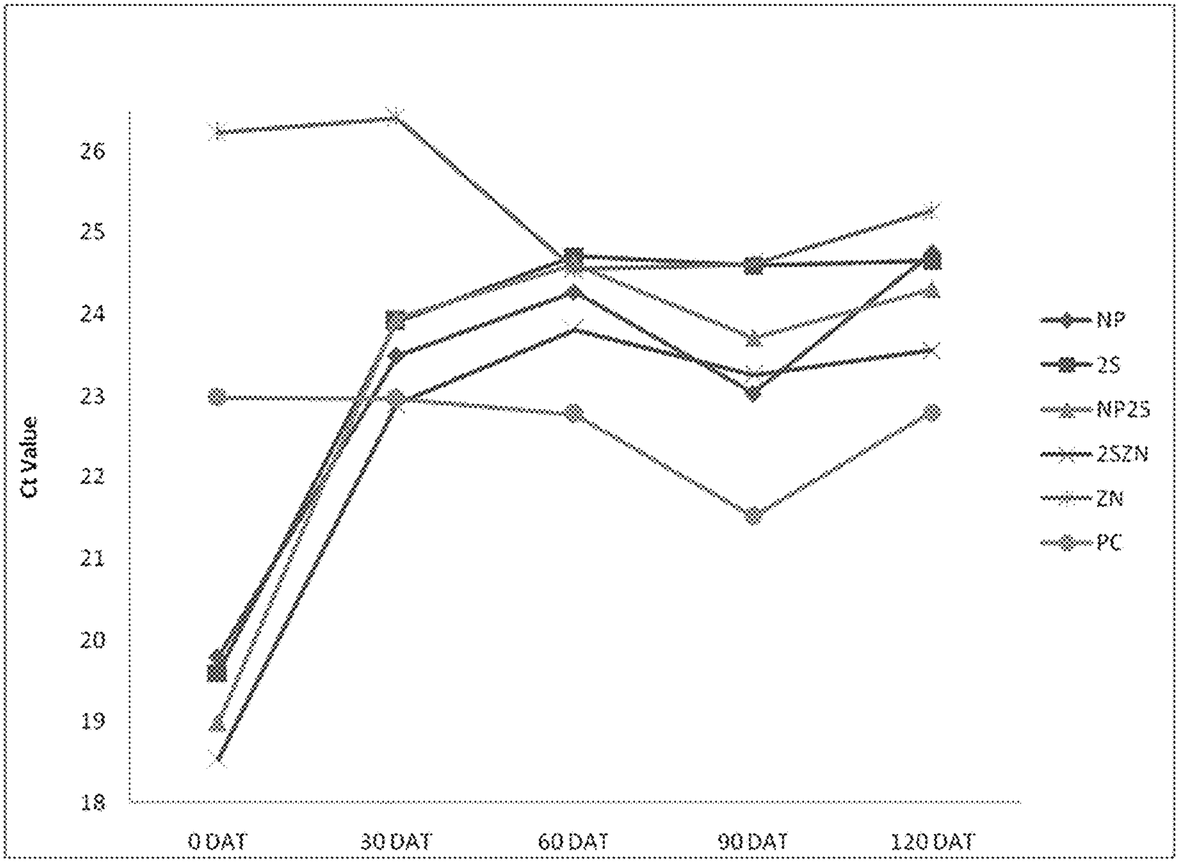
FIG. 9: is an example according to various embodiments illustrating shows the effect of different treatment on HLB titer 30, 60, 90, and 120 DAT, compared with positive control (untreated seedlings)

FIG. 8 is an example according to various embodiments illustrating the CLas titer of infected Mosambi plants before the treatment and at 30, 60, 90, 120 DAT with 2S albumin proteins plus Nano-ZnO compared with control plants (red color bars indicate without treatment whereas blue bars represent treated plants). FIG. 9 is an example according to various embodiments illustrating the effect of different treatment on HLB titer 30, 60, 90, and 120 DAT, compared with positive control (untreated seedlings).

The effects of 2S albumin protein and Nano-ZnO on CLas titer in infected *citrus* plant were determined. In addition to the individual treatment, the combined effect of both compounds at on CLas titer (FIG. 8) was monitored. The initial CLas load at 0 DAT was $4\times10^6$/12.5 ng of genomic DNA, while at 30 DAT (2S albumin plus Nano-ZnO at the ratio of 1:1) the CLas population reduced to $1.5\times10^5$. The rate of suppression of HLB titer is high in 2S albumin plus Nano-ZnO treatment as compared to individual treatments. This might be due to combined effect of both compounds on the growth and multiplication of CLas inside the phloem. It was observed that the bacterial titer reduced by 27, 41.69, 23 and 34.16-fold after 30, 60, 90 and 120 DAT respectively (Table 3). The comparative effectiveness of 2S albumin protein, Zinc nitrate, Nano-ZnO and the relevant controls are summarized (FIG. 9).

The treatments were: NP (Nano-ZnO), 2S (2S albumin protein alone), NP2S (Nano-ZnO plus 2S albumin proteins), 2SZN (2S albumin Protein plus Zinc nitrate), ZN (Zinc nitrate) and PC (Positive control only injected with PBS).

Discussion

HLB is economically the most serious and destructive disease of *citrus* and has severally affected the *citrus* industry as no other disease throughout the world. The rapid proliferation of CLas population in phloem tissue would deliver virulence factors and effector proteins into the phloem of HLB affected *citrus* plant causing malfunction of phloem tissue (i.e. cell death, necrosis and whole plant dieback). The CLas infection also leads to reduction in plant vigor, flowering and fruit yield. Because of the knowledge gap in complete understanding of CLas and its pathogenesis, there is difficulty in controlling CLas infection progression and development of management strategies to mitigate the pathogen's infection progression. Since CLas pathogen resides and restricted to the phloem, there are significant challenges in development of effective antimicrobial strategies. There are several reports, where certain antibiotics i.e. ampicillin, streptomycin may reduce the inoculums load of CLas, but owing to inconsistent effect, the commercial practice of these chemicals is very limited. Thus, major emphasis of this investigation was to explore the antimicrobial activity of the 2S albumin, a plant storage protein to induce microbial inhibition. The 2S albumin family protein, SiAMP2 from *Sesamum indicum* kernels was shown to possess antimicrobial properties. The 2S Albumin protein of ~16 kDa, from Seeds of *Wrightia tinctoria* showed antibacterial activity against human pathogen *Morexalla catarrhali*s. Thus, efforts were made to seek novel antimicrobials against CLas infection progression with different mechanisms of action.

Recently the 2S albumin protein has been characterized from the seeds of pumpkin (*Cucurbita maxima*) and *Putranjiva* (*Putranjiva roxburghii*), a heterodimeric protein of ~12 kDa, with RNase, DNase and antimicrobial activities. Recent interest in the application of engineered Nano-ZnO formulation to improve the immunity of different agricultural crops against bacterial and fungal pathogens has gained increased momentum. There are reports of the effective antibacterial activity of Nano-ZnO against *E. coli, P. aeruginosa* and *S. aureus*. This inhibitory effect of Nano-ZnO may be due to its ability to damage bacterial cell membrane and their consequent death. Use of Nano-ZnO as an effective antibacterial agent to protect *citrus* industry from destructive HLB has been suggested. According to various embodiments, the antibacterial attributes of 2S albumin protein and Nano-ZnO may be combined to treat CLas infection in Mosambi (*Citrus sinensis*) plants.

CLas titer was monitored during the experimental period using highly sensitive, specific and robust TaqMan-qPCR assay. Except Zinc nitrate treatment, inhibitory effect against CLas was observed with all four treatments. In the case of 2S albumin protein alone, the pathogen titer reduced gradually after each treatment. The reduction rate was very high initially at 94% of initial bacterial titer 30 DAT bacterium inoculums 30 DAT and 96.63%, 96.35%, 96.49% after 60, 90 and 120 days of treatment respectively. In other words, it was found that when 2S albumin protein was applied individually, there was more than 28-fold reduction of CLas titer after 60 days of treatment and no change observed after 120 days as compared to control plants (Table 3). It was also observed that Nano-ZnO treatment also suppressed CLas population. Overall effectiveness of Nano-ZnO was lower than 2S albumin protein as evidenced by their reduced copy number and pathogen titer (FIG. 7C). However, treatment of 2S albumin protein in combination with Nano-ZnO showed the highest reduction of CLas titer 30 DAT and sustained titer reduction even up to 120 DAT. A maximum of 41.69-fold decrease of bacterial titer after 60 days of treatment was recorded with the combined treatment at any given time (FIGS. 8, 9 and Table 3).

The strategy of combining 2S albumin with Nano-ZnO treatment, according to various embodiments, was successful in reducing CLas infection progression in phloem of Mosambi plants. The reduction of CLas titer was observed in treated plants in comparison with untreated control plants (statistically significant, $p<0.05$). The additive effect of 2S albumin and Nano-ZnO together with no observable adverse effect on the health of plants even ten months after trunk injection potentially could be used to mitigate the spread of CLas.

In summary, it has been demonstrated for the first time that antimicrobial 2S albumin protein in combination with Nano-ZnO significantly reduced CLas titer in HLB affected Mosambi plants in comparison to HLB affected untreated control. The actual mechanism of action of 2S protein and the 2S protein plus the Nano-ZnO remain to be determined. However, the antimicrobial property of Nano-ZnO is primarily attributed to the release of significant amounts of $Zn^{2+}$ ions locally due to large surface area to volume ratio of ultra-small size (<5 nm) particles. Other possibilities include direct interaction of Nano-ZnO to CLas, resulting in disruption of the cell membrane and causing oxidative stress, as well as binding interaction of Nano-ZnO to albumin. Additionally, NAC coated Nano-ZnO might have contributed as an efficient delivery of the 2S antimicrobial protein to the phloem for targeting CLas, significantly suppressing its population.

Nano-Zinc Oxide Characterization

Figure 10A:
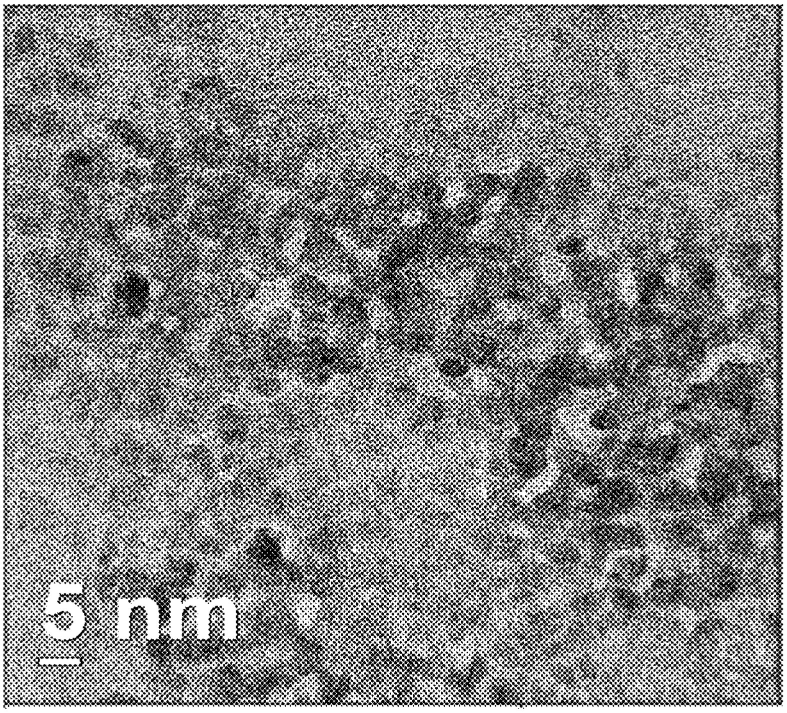
FIG. 10A: is an example according to various embodiments illustrating a HRTEM image of the synthesized Nano-ZnO.
Figure 10B:
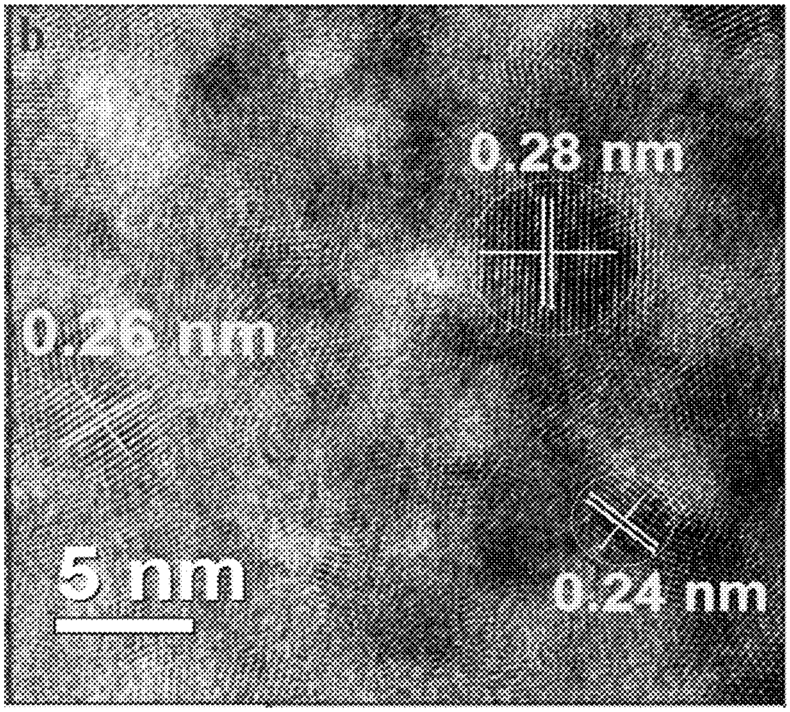
FIG. 10B: is an example according to various embodiments illustrating aHRTEM image of the synthesized Nano-ZnO.
Figure 10C:
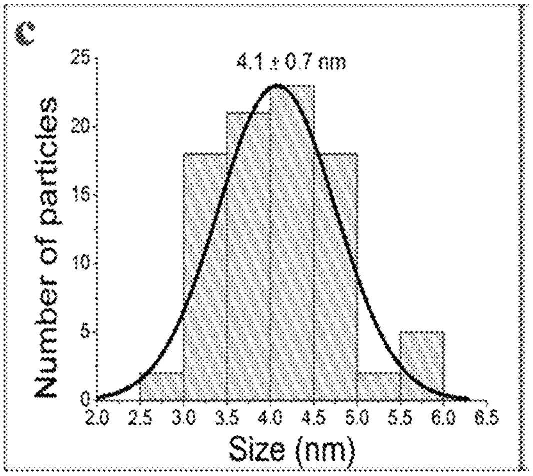
FIG. 10C: is an example according to various embodiments illustrating particle size distribution histogram calculated from HRTEM studies via processing 7 images and total number of 89 particles, the average size was found to be 4.1 nm±0.7 nm.
Figure 10D:
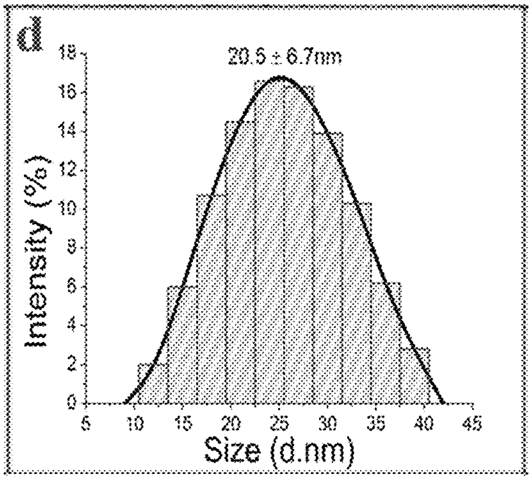
FIG. 10D: is an example according to various embodiments illustrating DLS histogram of particle size distribution.
Figure 10E:
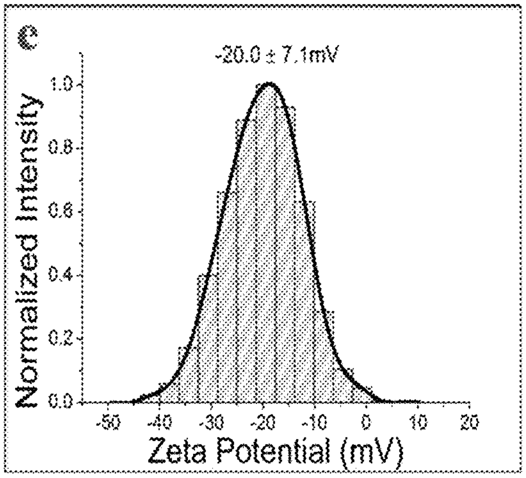
FIG. 10E: is an example according to various embodiments illustrating Zeta-potential (ζ) data.

HRTEM measurements were carried out to determine Nano-ZnO particle size, size distribution and the crystalline phase of synthesized particles. FIG. 10A and FIG. 1B are an examples according to various embodiments illustrating HRTEM images of the synthesized Nano-ZnO. FIG. 10C is an example according to various embodiments illustrating particle size distribution histogram calculated from HRTEM studies via processing 7 images and total number of 89 particles, the average size was found to be 4.1 nm±0.7 nm. FIG. 10D is an example according to various embodiments illustrating DLS histogram of particle size distribution, the average hydrodynamic diameter of Nano-ZnO is calculated to be about 20.5±6.7 nm. FIG. 10E is an example according to various embodiments illustrating Zeta-potential (ζ) data, the ζ value at pH 7.50 is estimated to be −20.0 mV±7.1 mV, confirming negative surface charge of Nano-ZnO More specifically, FIG. 10A shows representative HRTEM images of Nano-ZnO, showing particles in the size range 2.5 nm to 6 nm. HRTEM Selected Area Electron Diffraction (SAED) pattern revealed crystalline structures. The lattice spacing values were calculated from in FIG. 10B and they were found to be 0.24 nm, 0.26 nm and 0.28 nm corresponding to [1 0 1], [0 0 2] and [1 0 0] lattice planes, respectively for ZnO Wurtzite (JCPDS card #36-1451). HRTEM images were further analyzed to determine Nano-ZnO size distribution via processing multiple images obtained from the measurement (FIG. 10C), and the average size was found to be 4.1 nm±0.7 nm. To further understand the dispersion properties of Nano-ZnO in water, hydrodynamic size was determined via Dynamic Light Scattering (DLS) measurements (FIG. 10D). The average hydrodynamic size was found to be 20.5±6.7 nm (PDI: 0.129). The role of NAC coating was investigated via zeta potential measurements and zeta-potential value (ζ) −20.0±7.1 mV at pH 7.50 (FIG. 10E) was found. Negative zeta potential value is indicative of Nano-ZnO surface coating with NAC and the presence of negatively charged carboxyl group on the particle surface. Presence of larger size particles in the solution state as measured by the DLS is indicative of particle-particle interactions causing slight particle agglomeration at nearly neutral pH conditions.

Additional Supporting Information

FIGS. 11A, 11B, 11C, 11D, 11E, 11F, 11G, and 11H are an example according to various embodiments illustrating results of a phytotoxicity assessment that was carried out using vinca (vincire) plants (obtained from local Home Depot store), the images were taken after 72 hours of foliar application.

Figure 11A:
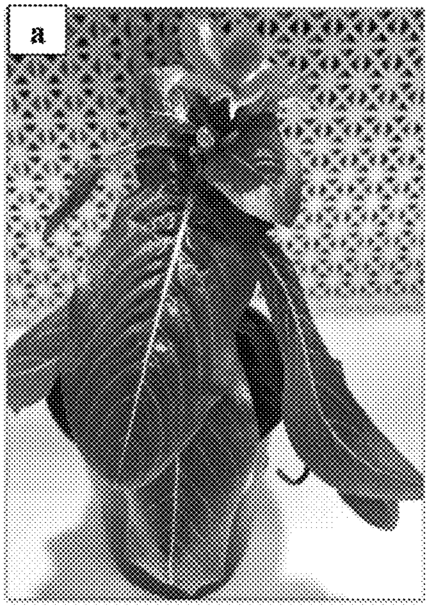
FIG. 11A: is an example according to various embodiments illustrating results of a phytotoxicity assessment on vinca (vincire) plants after 72 hours of foliar application of DI water.
Figure 11B:
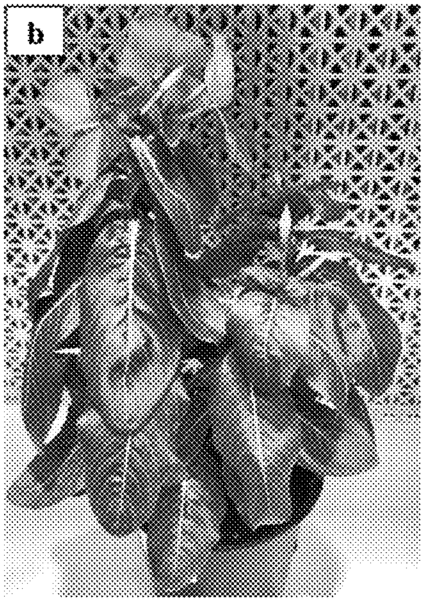
FIG. 11B: is an example according to various embodiments illustrating results of a phytotoxicity assessment on vinca (vincire) plants after 72 hours of foliar application of Nano-ZnO at 300 μg/ml.
Figure 11C:
FIG. 11C: is an example according to various embodiments illustrating results of a phytotoxicity assessment on vinca (vincire) plants after 72 hours of foliar application of Nano-ZnO at 600 μg/ml.
Figure 11D:
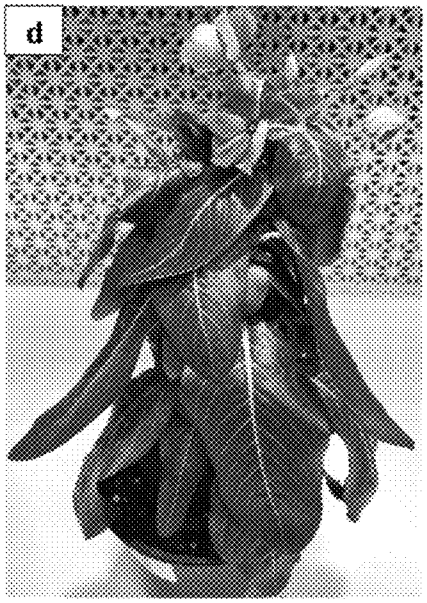
FIG. 11D: is an example according to various embodiments illustrating results of a phytotoxicity assessment on vinca (vincire) plants after 72 hours of foliar application of Nano-ZnO at 1,000 μg/ml.
Figure 11E:
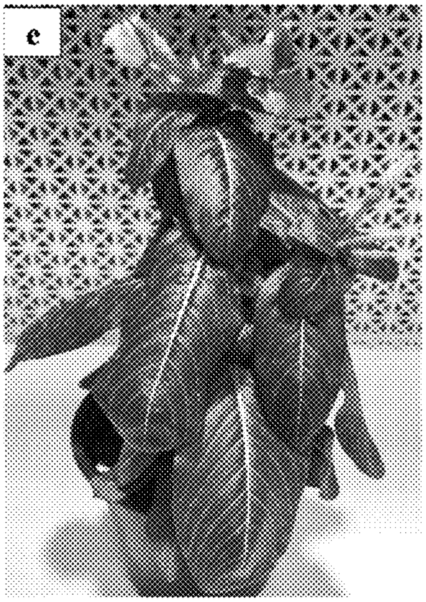
FIG. 11E: is an example according to various embodiments illustrating results of a phytotoxicity assessment on vinca (vincire) plants after 72 hours of foliar application of Zinc nitrate at 300 μg/ml.
Figure 11F:
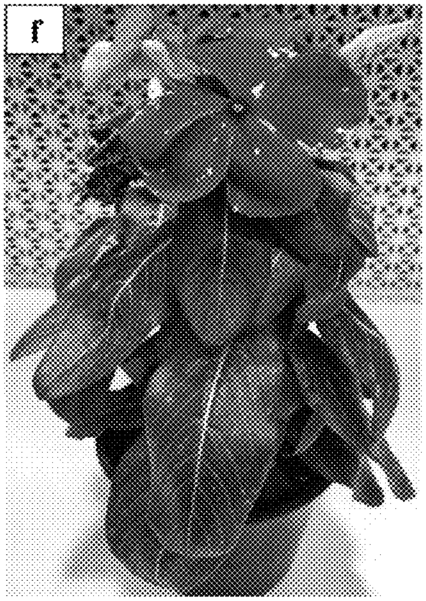
FIG. 11F: is an example according to various embodiments illustrating results of a phytotoxicity assessment on vinca (vincire) plants after 72 hours of foliar application of Zinc nitrate at 600 μg/ml.
Figure 11G:
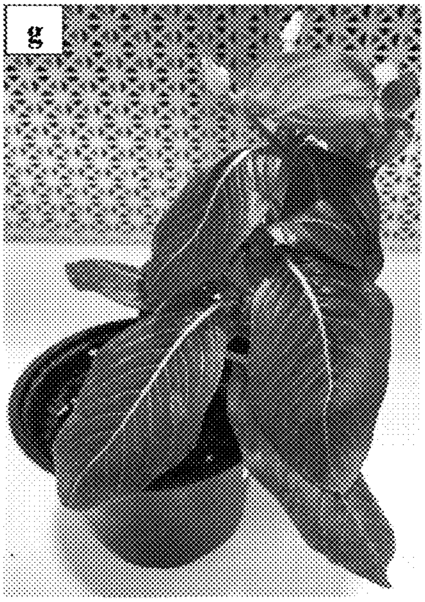
FIG. 11G: is an example according to various embodiments illustrating results of a phytotoxicity assessment on vinca (vincire) plants after 72 hours of foliar application of Zinc nitrate at 1,000 μg/ml.
Figure 11H:
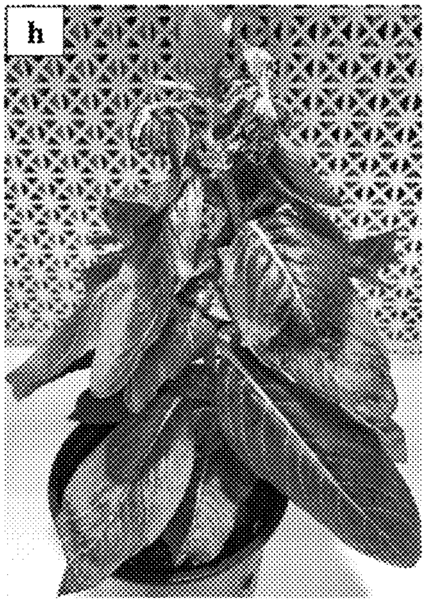
FIG. 11H: is an example according to various embodiments illustrating results of a phytotoxicity assessment on vinca (vincire) plants after 72 hours of foliar application of Copper nitrate at 1,000 μg/ml.

Phytotoxicity rating scale was assessed via Vinca plants treated with different concentrations of Nano-ZnO, zinc nitrate, DI water and copper nitrate. The assessment was done visually based on size and number of burns on plants after 72 hours of foliar application. Vinca (vincire) plant phytotoxicity rating on a scale of "−" non-phytotoxic, "+" minimal phytotoxic, "++" moderate phytotoxic, and (+++) heavy phytotoxic. As shown in FIG. 11A, DI water was non-phytotoxic as expected. As shown in FIG. 11B, Nano-ZnO at 300 μg/ml was found to be non-phytotoxic. As shown in FIG. 11C, Nano-ZnO at 600 μg/ml was found to be non-phytotoxic. As shown in FIG. 11D, Nano-ZnO at 1,000 μg/ml was found to be non-phytotoxic. As shown in FIG. 11E, Zinc nitrate at 300 μg/ml was found to be non-phytotoxic. As shown in FIG. 11F, Zinc nitrate at 600 μg/ml was found to be minimally phytotoxic. As shown in FIG. 11G Zinc nitrate at 1,000 μg/ml was found to be moderately phytotoxic. As shown in FIG. 11H, copper nitrate was found to be severely phytotoxic at 1,000 μg/ml.

High Resolution Transmission Electron Microscopy (HR-TEM)

A dilute nano-ZnO solution (25 ppm metallic Zn) was sonicated for 30 minutes using Elmasonic S30H sonic bath. 5 μL of the sonicated solution was drop-casted on a TEM grid (Electron Microscopy Sciences, catalogue #CF300-AU-UL) and air-dried overnight. The measurements were carried out via FEI Tecnai F30 TEM instrument. For generating a histogram of particle size distribution, the size of about 200 particles was measured from several HRTEM images using Gatan Microscopy Suite (GMS) 3 software. Fast Fourier Transform (FFT) analysis was done on HRTEM images to understand the crystalline phage of nano-ZnO. The lattice spacing distance (d-values, A°) obtained through FFT analysis were compared to Powder Diffraction Files (PDF) of various possible Zn related compounds reported to International Center for Diffraction Data (ICDD).

Dynamic Light Scattering (DLS) and Zeta Potential

DLS and zeta potential measurements were carried out at 25° C. in DI water using Malvern Zetaziser ZS90. DLS measurements were performed using disposable polystyrene cuvette (Malvern Company; product #DTS0012) and zeta potential measurements were performed using folded capillary zeta cells (Malvern; product #DTS1070). Nano-ZnO solution at 1000 ppm metallic Zinc concentration was vortex mixed and sonicated for around 5 minutes in order to fully disperse particles.

Table 4 shows phytotoxicity rating scale was assessed via Vinca plants treated with different concentrations of Nano-ZnO, zinc nitrate, DI water and copper nitrate. The assessment was done visually based on size and number of burns on plants after 72 hours of foliar application. Vinca (vincire) plant phytotoxicity rating on a scale of "–" non-phytotoxic, "+" minimal phytotoxic, "++" moderate phytotoxic, and (+++) heavy phytotoxic.

TABLE 4

| Materials tested | Metal concentration (μg/ml) | Phytotoxicity rating |
|---|---|---|
| DI water | NA | – |
| Nano-ZnO | 300 | – |
| | 600 | – |
| | 1000 | – |
| Zinc nitrate | 300 | – |
| | 600 | + |
| | 1000 | ++ |
| Copper nitrate | 1000 | +++ |

SOME CONCLUSIONS

This demonstration of the in planta efficacy of two anti-microbial compounds against CLas viz. 2S albumin (a plant-based protein), Nano-Zinc Oxide (Nano-ZnO) and their combinations. Application of 2S albumin and Nano-ZnO formulation alone or in various combinations showed marked reduction in CLas titers in affected plants as compared to untreated plants where the pathogen titers were approximately stable throughout the time course under screen house conditions. Among all five treatments, 2S albumin-Nano-ZnO formulation performed best and showed significant reduction of CLas titer. It also confirms the potency of 2S albumin-Nano-ZnO formulation as an anti-microbial treatment for suppressing CLas in planta and could potentially be developed as a novel anti CLas therapeutics to mitigate the HLB severity affecting the *citrus* industry worldwide.

What is claimed is:

1. An antimicrobial treatment composition for suppressing or preventing a plant pathogen in planta, the antimicrobial treatment composition comprising:

at least one particle, wherein the at least one particle comprises a core and a shell, wherein the core comprises ZnO, wherein the shell comprises N-Acetylcysteine (NAC); and at least one antimicrobial 2S-albumin protein disposed on the shell.

2. The antimicrobial treatment composition according to claim 1, wherein the plant pathogen comprises *Candidatus Liberibacter asiaticus* (CLas), *Candidatus Liberibacter africanus* (CLaf), *Candidatus Liberibacter americanus* (CLam), or a combination thereof.

3. The antimicrobial treatment composition according to claim 1, wherein the plant pathogen is CLas.

4. The antimicrobial treatment composition according to claim 1, wherein the at least one particle has a size of less than about 10 nanometers.

5. A method for suppressing or preventing a plant pathogen in planta comprising administering an effective amount of the antimicrobial treatment composition according to claim 1.

6. The method according to claim 5, wherein the plant pathogen is CLas.

* * * * *